United States Patent
Carter

(10) Patent No.: US 6,596,535 B1
(45) Date of Patent: Jul. 22, 2003

(54) METABOLICALLY ACTIVATED RECOMBINANT VIRAL VECTORS AND METHODS FOR THE PREPARATION AND USE

(75) Inventor: Barrie J. Carter, Seattle, WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

(21) Appl. No.: 09/634,126

(22) Filed: Aug. 8, 2000

Related U.S. Application Data

(60) Provisional application No. 60/160,080, filed on Aug. 9, 1999.

(51) Int. Cl.$^7$ .............................................. C12N 15/00
(52) U.S. Cl. .................. 435/320.1; 424/93.2; 424/93.6; 435/69.1; 435/325; 435/455; 435/456; 435/457; 536/23.1; 536/23.72; 536/24.3
(58) Field of Search ............................... 424/93.2, 93.6; 435/69.1, 320.1, 325, 366, 371, 455, 456, 457, 462, 463; 536/23.72, 24.3, 23.1

(56) References Cited

U.S. PATENT DOCUMENTS

| | | | |
|---|---|---|---|
| 5,173,414 A | 12/1992 | Lebkowski et al. | 435/172.3 |
| 5,399,346 A | 3/1995 | Anderson et al. | 424/93.21 |
| 5,478,745 A | 12/1995 | Samulski et al. | 435/320.1 |
| 5,587,308 A | 12/1996 | Carter et al. | 435/240.2 |
| 5,605,690 A | 2/1997 | Jacobs et al. | 424/134.1 |
| 5,658,776 A | 8/1997 | Flotte et al. | 435/172.3 |
| 5,658,785 A | 8/1997 | Johnson | 435/367 |
| 5,677,158 A * | 10/1997 | Zhou et al. | 435/235.1 |
| 5,753,500 A | 5/1998 | Shenk et al. | 435/320.1 |
| 5,756,283 A | 5/1998 | Wilson et al. | 435/5 |
| 5,786,211 A | 7/1998 | Johnson | |
| 5,837,484 A | 11/1998 | Trempe et al. | 435/69.1 |
| 5,858,775 A | 1/1999 | Johnson | 435/320.1 |
| 5,866,696 A | 2/1999 | Carter et al. | |
| 5,869,305 A * | 2/1999 | Samulski et al. | 435/320.1 |
| 5,989,540 A | 11/1999 | Carter et al. | |
| 5,990,279 A | 11/1999 | Carter et al. | |
| 6,165,781 A | 12/2000 | Carter et al. | |

FOREIGN PATENT DOCUMENTS

| | | |
|---|---|---|
| WO | WO 95/13365 | 5/1995 |
| WO | WO 95/13392 | 5/1995 |
| WO | WO 96/17947 | 6/1996 |
| WO | WO 96/39530 A3 | 12/1996 |
| WO | WO 96/39530 A2 | 12/1996 |
| WO | WO 97/17458 | 5/1997 |
| WO | WO 97/32990 | 9/1997 |
| WO | WO 98/27204 | 6/1998 |
| WO | WO 98/27207 | 6/1998 |
| WO | WO 99/11764 | 3/1999 |
| WO | WO 99/20773 | 4/1999 |
| WO | WO 99/20779 | 4/1999 |
| WO | WO 00/14205 | 3/2000 |
| WO | WO 00/65038 | 11/2000 |
| WO | WO 00/73481 | 12/2000 |

OTHER PUBLICATIONS

Balagué, C. et al. (Apr. 1997). "Adeno–Associated Virus Rep78 Protein and Terminal Repeats Enhance Integration of DNA Sequences Into the Cellular Genome," *J. Virol.* 71(4):3299–3306.

Ferrari, F.K. et al. (Nov. 1997). "New Developments in the Generation of Ad–Free, High–Titer rAAV Gene Therapy Vectors," *Nature Med.* 3(11):1295–1297.

Flotte, T.R. et al. (Feb. 15, 1993). "Expression of the Cystic Fibrosis Transmembrane Conductance Regulator from a Novel Adeno–Associated Virus Promoter," *J. Biol. Chem.* 268(5):3781–3790.

Sanlioglu, S. Et al. (Mar. 1, 1999). "Two Independent Pathways for Recombinant Adeno–Associated Virus Genome Conversion Occur After UV–C and E4orf6 Augmentation of Transduction," *Hum. Gene Ther.* 10:591–602.

Urcelay, E. et al. (Apr. 1995). "Asymmetric Replication In Vitro from a Human Sequence Element is Dependent on Adeno–Associated Virus Rep Protein," *J. Virol.* 69(4):2038–2046.

Atkinson E. M. et al. (1998). "A High–Throughput Hybridization Method For Titer Determination Of Viruses and Gene Therapy Vectors," *Nucleic Acids Res.* 26(11):2821–2823.

Bantel–Schaal, U. et al. (1988). "Adeno–Associated Viruses Inhibit Sv40 DNA Amplification and Replication Of Herpes Simplex Virus In Sv40–Transformed Hamster Cells," *Virology* 164:64–74.

Bantel–Schaal, U. et al. (1988). "Dissociation Of Carcinogen–Induced Sv40 DNA–Amplification and Amplification Of AAV DNA In A Chinese Hamster Cell Line," *Virology* 166:113–122.

Berns, K. I. (1995). "Hepatitis B Virus," Chapter 77 In *Virology*, vol. 2, Raven Press, New York pp. 2173–2197.

Berns (1995). "Parvoviridae and Their Replication," Chapter 62 In *Virology*, vol. 2, Raven Press, New York pp. 1743–1763.

Carter, B. J. (1983). "Variant and Defective Interfering Parvoviruses," Chapter 6 In *The Parvoviruses*. K. I. Berns, ed., Plenum Press, New York, pp. 209–258.

Carter, B. J. (1989). "Adeno–Associated Virus Helper Functions," Chapter 13 In *Handbook of Parvoviruses* vol. I, pp. 169–228.

Carter, B. J. (1992). "Adeno–Associated Virus Vectors," *Curr. Op. Biotechnol.* 3:533–539.

(List continued on next page.)

Primary Examiner—James Housel
Assistant Examiner—Ulrike Winkler
(74) Attorney, Agent, or Firm—Morrison & Foerster LLP

(57) ABSTRACT

Recombinant viral vectors, especially parvovirus vectors such as adeno-associated virus (AAV) vectors, capable of enhanced expression of heterologous sequences, and methods for their construction and use, are provided. The vectors have a structure, or are capable of rapidly adopting a structure, which involves intrastrand base pairing of at least one region in a heterologous sequence.

29 Claims, 11 Drawing Sheets

OTHER PUBLICATIONS

Clark, K. R.et al. (1995). "Cell Lines For The Production Of Recombinant Adeno–Associated Virus," *Hum. Gene Therapy* 6:1329–1341.

Cromartie, W. J. et al. (1977). "Arthritis In Rats After Systemic Injection Of Streptococcal Cells Or Cell Walls," *J. Exp. Med.* 146:1585–1602.

De la Maza, L. M. and Carter, B. J. (1980). "Molecular Structure Of Adeno–Associated Virus Variant DNA," *J. Biol. Chem.* 255:3194–3203.

Dong, J. Y. et al. (1996). "Quantitative Analysis Of The Packaging Capacity Of Recombinant Adeno–Associated Virus," *Hum. Gene Therapy* 7:2101–2112.

Ferrari, F. K. et al. (1996). "Second–Strand Synthesis Is A Rate–Limiting Step For Efficient Transduction By Recombinant Adeno–Associated Virus Vectors," *J. Virol.* 70:3227–3234.

Fisher, K. J. et al. (1996). "Transduction With Recombinant Adeno–Associated Virus For Gene Therapy Is Limited By Leading–Strand Synthesis," *J. Virol.* 70:520–532.

Flotte, T. R. and Carter, B. J. (1995). "Adeno–Associated Virus Vectors For Gene Therapy," *Gene Therapy* 2:357–362.

Flotte, T. R. et al. (1992). "Gene Expression From Adeno–Associated Virus Vectors In Airway Epithelial Cells, "*Am. J. Respir. Cell. Mol. Biol.* 7:349–356.

Hauswirth, W. W. and Berns, K. I. (1979). "Adeno–Associated Virus DNA Replication: Nonunit–Length Molecules," *Virology* 93:57–68.

Hermonat, P. L. et al. (1984). "Genetics Of Adeno–Associated Virus: Isolation and Preliminary Characterization Of Adeno–Associated Virus Type 2 Mutants," *J. Virol.* 51:329–339.

Hermonat, P. L. and Muzyczka, N. (1984). "Use Of Adeno–Associated Virus As A Mammalian DNA Cloning Vector: Transduction Of Neomycin Resistance Into Mammalian Tissue Culture Cells," *Proc. Natl. Acad. Sci. USA*, 81:6466.

Lebkowski, J. S. et al. (1988). "Adeno–Associated Virus: A Vector System For Efficient Introduction and Integration Of DNA Into A Variety Of Mammalian Cell Types," *Mol. Cell. Biol.*8(10):3988–3996.

Lynch, C. M. et al. (1977). "Adeno–Associated Virus Vectors For Vascular Gene Delivery," *Circ. Res.* 80:497–505.

McLaughlin, S. K. et al. (1988). "Adeno–Associated Virus General Transduction Vectors: Analysis Of Provirual Structures," *J. Virol.* 62:1963.

Muzyczka, N. (1992). "Use Of Adeno–Associated Virus As A General Transduction Vector For Mammalian Cells," *Curr. Top. Microbiol. Immunol.* 158:97–129.

Russell, J. et al. (1995). "Cis–Acting Components Of Human Papillomavirus (Hpv) Dna Replication: Linker Substitution Analysis Of The Hpv Type 11 Origin," *J. Virol.* 69(2):651–660.

Samulski, R. J. et al. (1989). "Helper–Free Stocks Of Recombinant Adeno–Associated Viruses: Normal Integration Does Not Require Viral Gene Expression," *J. Virol.* 63:3822–3828.

Srivastava, A. et al. (1983). "Nucleotide Sequence and Organization Of The Adeno–Associated Virus 2 Genome," *J. Virol.* 45:555–564.

Tratschin, J. et al. (1984). "Genetic Analysis Of Adeno–Associated Virus: Properties Of Deletion Mutants Constructed In Vitro and Evidence For An Adeno–Associated Virus Replication Function," *J. Virol.* 51:611–619.

Tratschin, J. et al. (1984). "A Human Parvovirus, Adeno–Associated Virus, As A Eucaryotic Vector: Transient Expression and Encasidation Of The Procaryotic Gene For Chloramphenicol Acetyltransferase," *Mol. Cell. Biol.* 4:2072–2081.

Tratschin, J. et al. (1985). "Adeno–Associated Virus Vector For High–Frequency Integration, Expression and Rescue Of Genes In Mammalian Cells," *Mol. Cell. Biol.* 5(11):3251–3260.

Yakobson, B. et al. (1987). "Replication Of Adeno–Associated Virus In Synchronized Cells Without The Addition Of A Helper Virus," *J. Virol.* 61:972–987.

Yakobson, B. et al. (1988). "Replication Of Adeno–Associated Virus In Cells Irradiated With Uv Light At 254nm," *J. Virol.* 63:1023–1030.

Yalkinoglu, A. O. et al. (1988). "DNA Amplification Of Adeno–Associated Virus As A Response To Cellular Genotoxic Stress," *Cancer Res.* 48:3123–3125.

\* cited by examiner

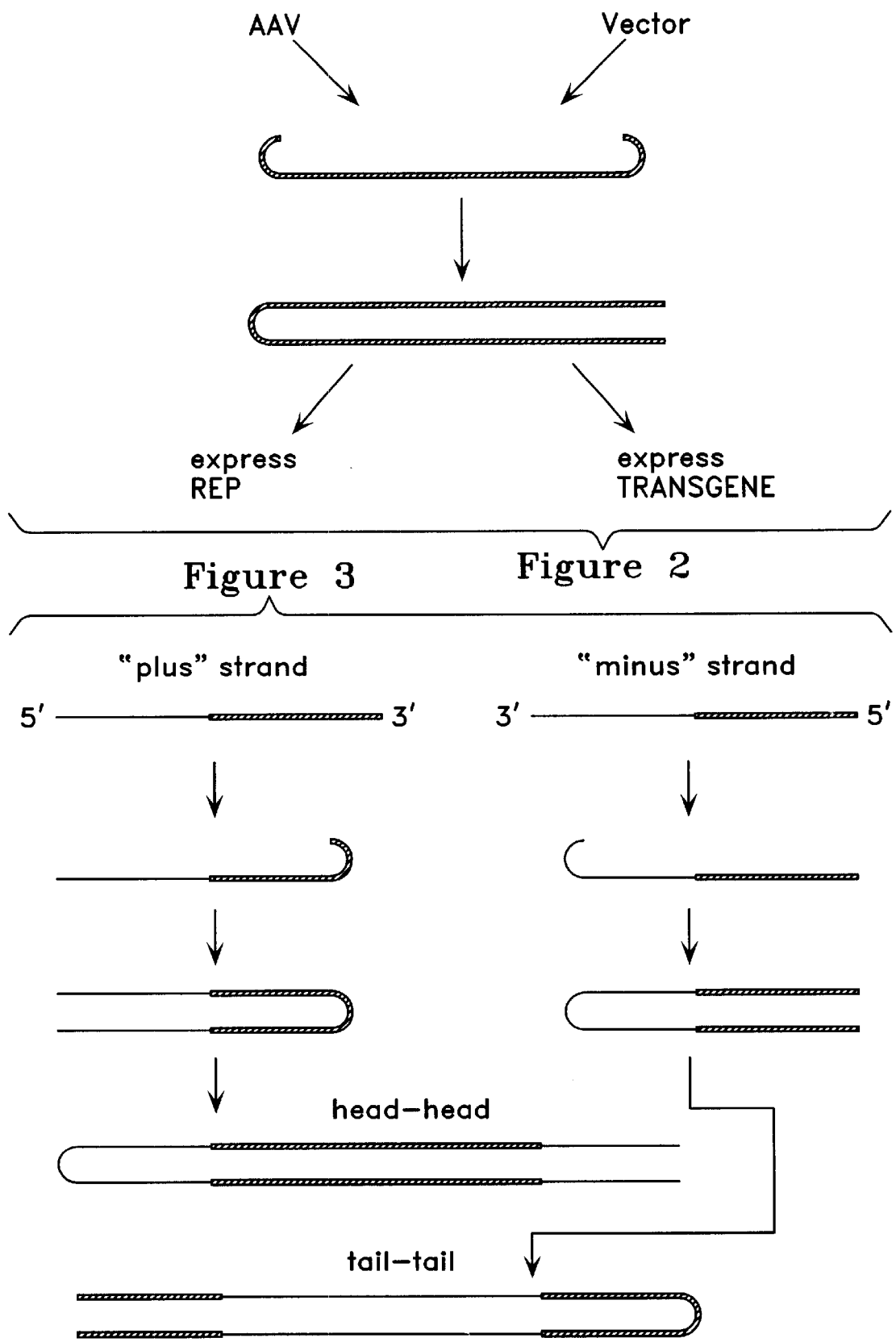

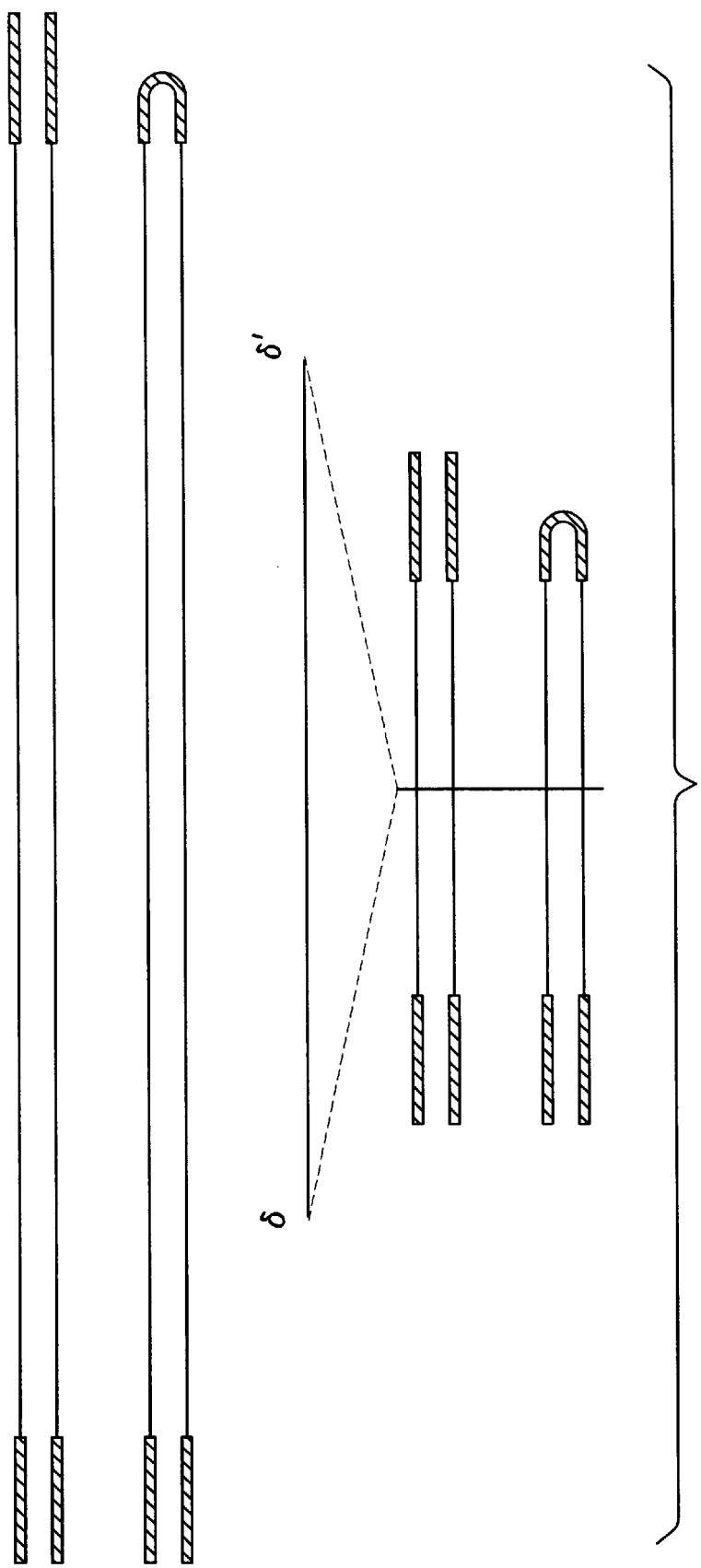

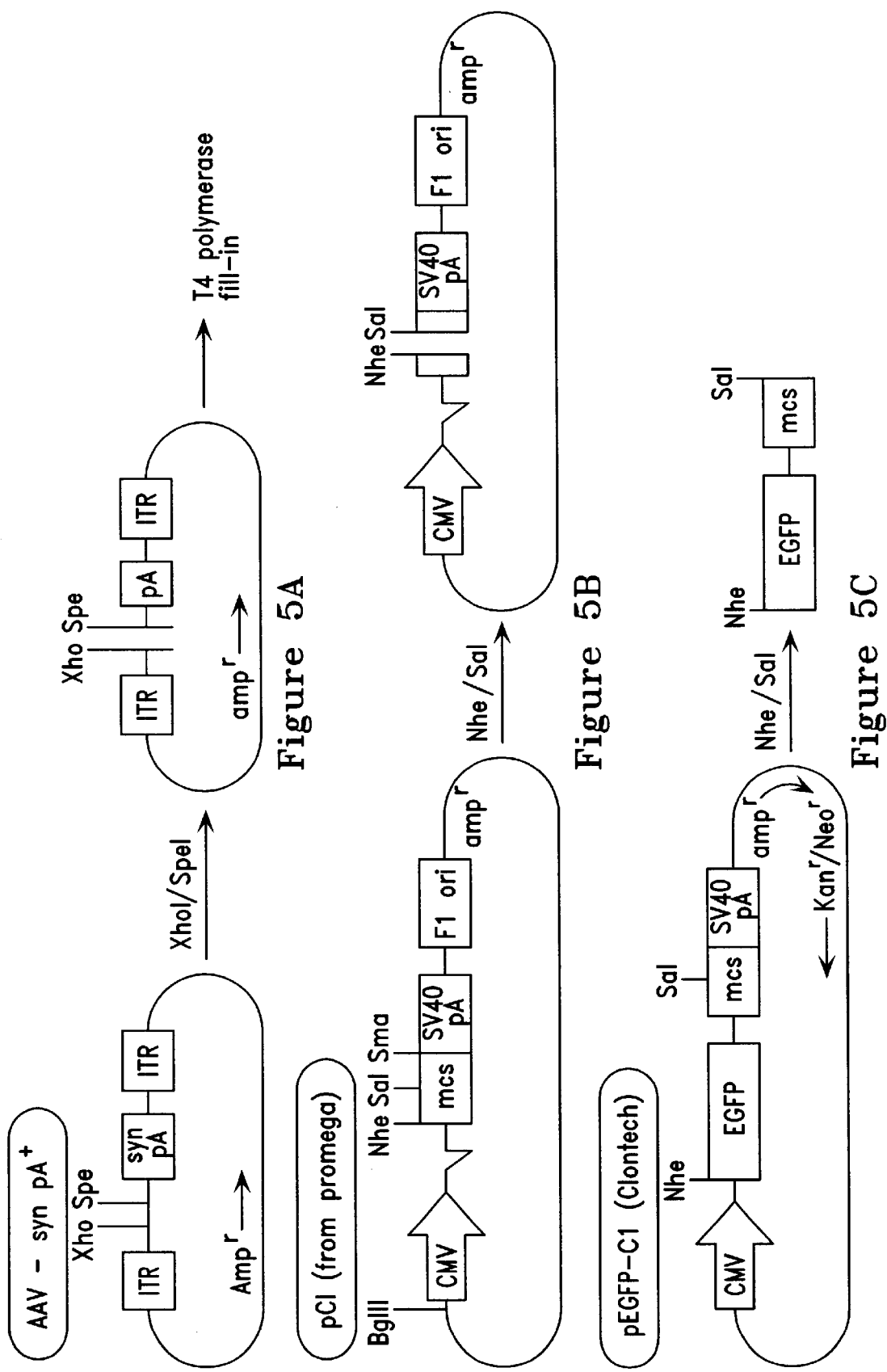

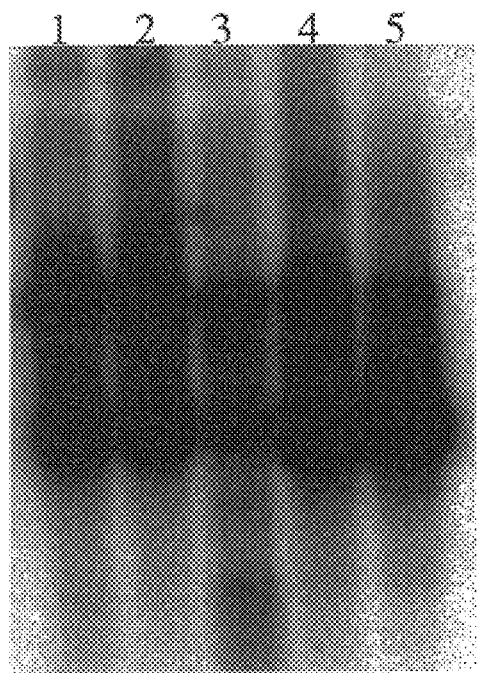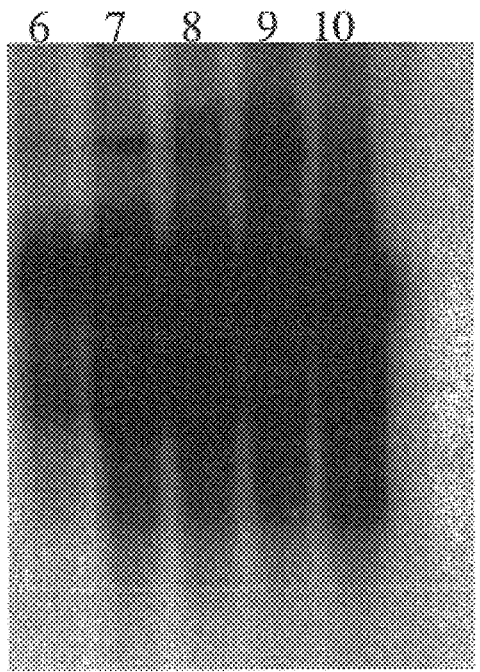
Figure 9A
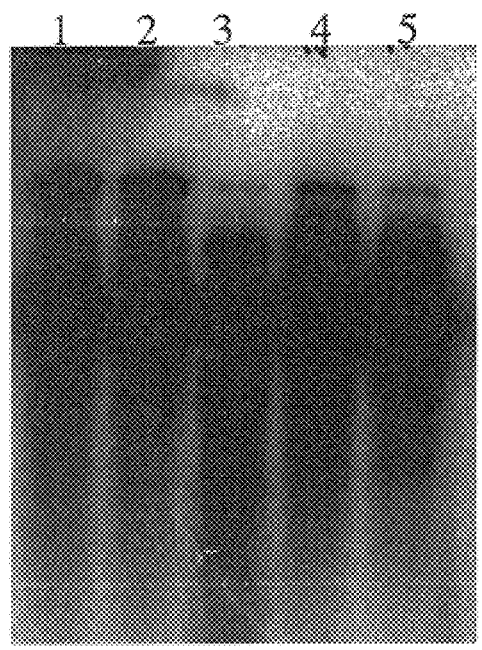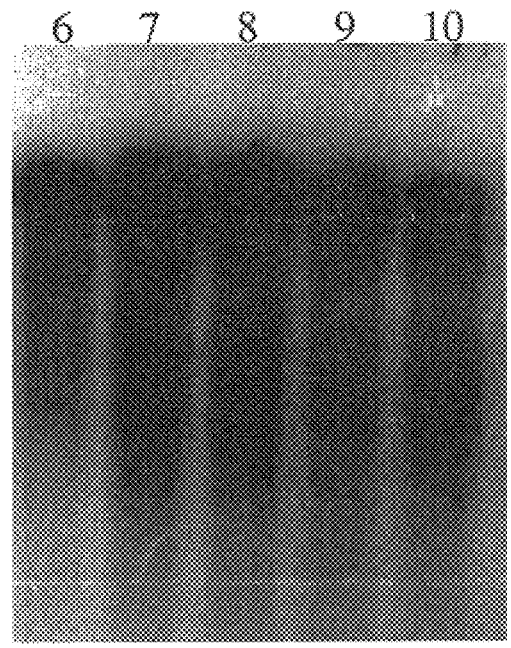
Figure 9B

AlaArgGlnAlaAlaTrpArgGluGlyAlaGlyLeuArgGlyArgGlu
GlyAlaArgAlaGlyGlyAsnArgThrProProAlaSerMetAlaPro
ValAlaValTrpAlaAlaLeuAlaValGlyLeuGluLeuTrpAlaAla
AlaHisAlaLeuProAlaGlnValAlaPheThrProTyrAlaProGlu
ProGlySerThrCysArgLeuArgGluTyrTyrAspGlnThrAlaGln
MetCysCysSerLysCysSerProGlyGlnHisAlaLysValPheCys
ThrLysThrSerAspThrValCysAspSerCysGluAspSerThrTyr
ThrGlnLeuTrpAsnTrpValProGluCysLeuSerCysGlySerArg
CysSerSerAspGlnValGluThrGlnAlaCysThrArgGluGlnAsn
ArgIleCysThrCysArgProGlyTrpTyrCysAlaLeuSerLysGln
GluGlyCysArgLeuCysAlaProLeuArgLysCysArgProGlyPhe
GlyValAlaArgProGlyThrGluThrSerAspValValCysLysPro
CysAlaProGlyThrPheSerAsnThrThrSerSerThrAspIleCys
ArgProHisGlnIleCysAsnValValAlaIleProGlyAsnAlaSer
MetAspAlaValCysThrSerThrSerProThrArgSerMetAlaPro
GlyAlaValHisLeuProGlnProValSerThrArgSerGlnHisThr
GlnProThrProGluProSerThrAlaProSerThrSerPheLeuLeu
ProMetGlyProSerProProAlaGluGlySerThrGlyAspGluPro
LysSerCysAspLysThrHisThrCysProProCysProAlaProGlu
LeuLeuGlyGlyProSerValPheLeuPheProProLysProLysAsp
ThrLeuMetIleSerArgThrProGluValThrCysValValValAsp
ValSerHisGluAspProGluValLysPheAsnTrpTyrValAspGly
ValGluValHisAsnAlaLysThrLysProArgGluGluGlnTyrAsn
SerThrTyrArgValValSerValLeuThrValLeuHisGlnAspTrp
LeuAsnGlyLysAspTyrLysCysLysValSerAsnLysAlaLeuPro
AlaProMetGlnLysThrIleSerLysAlaLysGlyGlnProArgGlu
ProGlnValTyrThrLeuProProSerArgAspGluLeuThrLysAsn
GlnValSerLeuThrCysLeuValLysGlyPheTyrProArgHisIle
AlaValGluTrpGluSerAsnGlyGlnProGluAsnAsnTyrLysThr
ThrProProValLeuAspSerAspGlySerPhePheLeuTyrSerLys
LeuThrValAspLysSerArgTrpGlnGlnGlyAsnValPheSerCys
SerValMetHisGluAlaLeuHisAsnHisTyrThrGlnLysSerLeu
SerLeuSerProGlyLys

Figure 10

METABOLICALLY ACTIVATED RECOMBINANT VIRAL VECTORS AND METHODS FOR THE PREPARATION AND USE

CROSS-REFERENCE TO RELATED APPLICATIONS

This application claims priority to U.S. provisional application No. 60/160,080 converted from U.S. patent application Ser. No. 09/370,454), filed Aug. 9, 1999, which is incorporated by reference in its entirety.

STATEMENT OF RIGHTS TO INVENTIONS MADE UNDER FEDERALLY SPONSORED RESEARCH

Not applicable.

TECHNICAL FIELD

The invention is in the field of viral constructs for gene delivery, in particular recombinant viral vectors, such as adeno-associated virus (AAV) vectors, for use in gene therapy and genomics screening.

BACKGROUND

Recombinant vectors based on parvovirus, such as adeno-associated virus (AAV), show promise for gene therapy. However, obtaining efficient, sufficient levels of expression of a transgene in various cell types has presented problems. Some cell types are impermissive in the sense that initiation of transcription or translation of the transgene is inefficient, with expression accordingly very slow to initiate, if it initiates at all. Yet in many contexts it is desirable to achieve sufficiently rapid expression.

Parvoviruses are small, encapisdated, single-stranded DNA viruses, the DNA genome of which is flanked by inverted terminal repeat (ITR) sequences. The DNA genome of parvoviruses encode for proteins required for replication (Rep) and encapsidation (Cap). Adeno-associated virus (AAV) is a defective parovirus that replicates only in cells in which certain functions, called "helper functions" are provided. Usually these functions are provided by helper virus infection. General reviews of parvovirus, including AAV, may be found in, for example, Carter (1989) *Handbook of Parvoviruses*; Berns (1995) *Virology*, Vol. 2, Raven Press, New York pages 2173–2197; Carter et al. (1983) In "The Parvoviruses" (K. I. Berns, ed.) Plenum Press, New York; Berns.

The native AAV genome is a linear single-stranded DNA molecule of approximately 4,675 nucleotides. Srivastava et al. (1983) *J. Virol.* 45:555–564. The native AAV genome contains sequences encoding Rep and Cap proteins (the rep and cap genes, respectively) flanked by an inverted terminal repeat (ITR) sequence of 145 nucleotides. Hermonat et al. (1984) *J. Virol.* 51:329–339; and Tratschin et al. (1984) *J. Virol.* 51:611–619. The life cycle of AAV is presented below. The life cycle of other parvoviruses is similar, with the exception that other parvoviruses do not require helper functions for replication (except to the extent they could require a host cell to go into S phase).

AAV Life Cycle

In outline, a productive AAV infective cycle in a cell which has been infected with a second, helper virus (or in a cell in which helper functions are present) proceeds as follows (see FIG. 1). Adsorption of AAV to a host cell is followed by inserting the single-stranded viral genome in a process generally known in the art as "transduction". In the presence of certain host cell functions related to replication (such as DNA polymerases), the incoming single-stranded viral genome is converted to a double-stranded replicative form. See FIG. 2. Initiation of this single-strand to double-strand (SS→DS) conversion is believed to involve formation of a hairpin structure by sequences within the AAV ITR, which generates a template-primer structure from which initiation of DNA replication can proceed. The product of this SS→DS conversion, the replicative form (RF), is a self-complementary double-stranded molecule that is covalently closed at one end (the end at which replication was initiated). See FIG. 3. The RF is thus a double-stranded molecule having the same sequence complexity, but approximately twice the molecular weight, of the incoming AAV genome (i.e., for a native genome of approximately 4.7 kilobases, the RF will have a molecular weight corresponding to 4.7 kilobase pairs). Although formation of a terminal hairpin to prime replication is believed to occur rapidly, the extension of this hairpin to form the double-stranded RF is postulated to be one of the rate-limiting steps in AAV replication. This process of RF generation can occur in the absence of helper function but is believed to be enhanced by helper function. See Carter, B. et al. (1990) vol. 1, pp. 169–226 and 255–282. Cells that are capable of producing AAV progeny are generally considered by those skilled in the art as "permissive" cells, and this process of conversion to double-stranded template is also known as "metabolic activation".

Subsequent to its formation, the RF is replicated to generate progeny RFs, in a process facilitated by AAV rep gene products and certain helper functions (see below). In addition, the RF serves as template for the formation of progeny AAV genomes, which are packaged into virus particles. These genomes are single-stranded DNA molecules of approximately 4.7 kb and represent both polarities as found in the double-stranded RF molecule.

In addition to being necessary for the synthesis of progeny AAV genomes, formation of the RF is required for transcription of viral proteins (or, in the case of recombinant AAV, the transcription of heterologous sequences such as a transgene) to occur, since cellular RNA polymerizing systems require a double-stranded template. Transcription of the AAV rep and cap genes results in production of Rep and Cap proteins. The viral Rep proteins facilitate amplification of the RF, generation of progeny viral genomes and may also play a role in viral transcriptional regulation. The viral Cap proteins are the structural proteins of the viral capsid. Single-stranded progeny viral genomes of both polarities are encapsidated into daughter virus particles, which are then released from the host cell.

Helper functions involved in the replication of the RF, as described above, can be provided by co-infection of AAV-infected cells with adenoviruses, herpesviruses or poxviruses. Carter (1990) supra. Alternatively, cells may contain integrated genes, viral or otherwise, that supply helper function. In addition, the requirement for helper function can sometimes be bypassed by treatment of AAV-infected cells with chemical and/or physical agents, such as hydroxyurea, ultraviolet irradiation, X-irradiation or gamma irradiation, for example, that may induce cellular repair, recombination and/or replication systems, or may otherwise affect cellular DNA metabolism. Yakobson et al. (1987) *J. Virol.* 61:972–987; Yakobson et al. (1988) *J. Virol.* 63:1023–1030; Bantel-Schaal, U. et al. (1988) *Virology* 164:64–74; Bantel- Schaal, U. et al. (1988) *Virology* 166:113–122; and Yalkinoglu et al. (1988) *Cancer Res.* 48:3123–3125. Although replication of the RF can occur, to some extent, in the absence of helper function; in general, this process is slow and/or inefficient in the absence of helper function.

De la Maza and Carter (1980) *J. Biol. Chem.* 255:3194–3203 describe variant AAV DNA molecules, obtained from AAV particles. Some of these molecules are less than unit length and display properties suggesting that they possess regions of self-complementarity. Hauswirth and Bems (1979) *Virology* 93:57–68 describe similar variant molecules obtained from AAV-infected cells. See FIG. 4. These molecules did not contain heterologous sequences; consequently their ability to express a heterologous sequence could not be evaluated.

Recombinant AAV Vectors and Viruses

The native AAV genome has been used as the basis of vector systems for the delivery and expression of heterologous genes in host cells such as mammalian cells, such as for gene therapy. Muzyczka (1992) *Curr. Top. Microbiol. Immunol.* 158:97–129; Carter, B. J. (1992) *Curr. Op. Biotechnol.* 3:535–539; and Flotte et al. (1995) *Gene Therapy* 2:357–362. Recombinant AAV (RAAV) vectors, based on the native AAV genome, are generally produced by deletion of rep and/or cap sequences and replacement by a heterologous sequence. Thus rAAV vectors generally comprise a single-stranded DNA molecule comprising a heterologous gene sequence or sequences flanked by at least one AAV ITR, and typically by two AAV ITRs, one at each end. Additional sequences involved in regulation of expression of the heterologous sequence, such as promoters, splice sites, introns, sequences related to mRNA transport and stability, polyadenylation signals and ribosomal binding sites, can also be included in rAAV vectors.

rAAV vectors can be encapsidated into AAV virus particles to form recombinant adeno-associated viruses (rAAV). In general, efficient, productive packaging in an AAV virus particle is limited to vectors having approximately the size of an AAV genome (i.e., approximately 4.7 kb) or smaller; although sequences having a length up to approximately 5,200 nucleotides can be packaged into AAV virus particles.

In one study of the effect of genome length on packaging efficiency, rAAV genomes having sizes between 2 kb and 6 kb were compared. Dong et al. (1996) *Hum. Gene Therapy* 7:2101–2112, it was observed that vectors having sizes between approximately 2 and approximately 6 kb were packaged into virus particles with similar efficiency, but viruses containing vector molecules with lengths greater than 5.2 kb were not infectious. In addition, evidence was obtained in the aforementioned study that was consistent with the idea that two vector molecules could be packaged into a single virus particle, if the vectors were less than half the size of a native AAV genome. Further speculation as to the ability of such short vectors to form double-stranded molecules inside the virion was presented. Expression levels of a chloramphenicol acetyl transferase (CAT) transgene were equivalent for genome-size vectors containing a single strand of vector DNA and for the short vectors, which were thought to contain double-stranded vector genomes and produced higher levels of vector DNA in infected cells. These results indicated that neither reduction in vector size, nor presence of potentially double-stranded vector DNA, had significant effects on expression levels.

Both the rAAV vectors and rAAV virus particles containing rAAV vectors can be used to express various heterologous gene products in host cells by transformation or transduction, respectively. The expression levels achieved by such vectors are affected by the same factors which influence the replication and transcription of native AAV. Thus, after infection of a host cell by a rAAV, rapid formation of a terminal hairpin can occur, but elongation of the hairpin to form a RF proceeds much more slowly. Ferrari et al. (1996) *J. Virol.* 70:3227–3234; and Fisher et al. (1996) *J. Virol.* 70:520–532.

Trying to achieve efficient, maximal levels of expression of heterologous sequences from rAAV has been hindered for several reasons. Expression of a heterologous sequence by a rAAV vector is maximal in a cell that is infected with a helper virus, expresses helper function, or has been treated with an agent that mimics helper function by affecting cellular DNA metabolism. Russell et al. (1995) *J. Virol.* 68:5719–5723; Ferrari et al., supra; and Fisher et al., supra. For gene therapy applications, infection of the host cell with a helper virus may be undesirable because of safety concerns related to other properties of helper viruses and helper functions. Treatment of cells with agents that mimic helper cell function may also be undesirable because of additional nonspecific effects and/or potential toxicity. Furthermore, provision of helper function by these agents may only be effective for infection with wild-type AAV.

Furthermore, AAV Rep protein functions are required for maximal expression of a heterologous sequence encoded by an rAAV vector. Since rAAV vectors generally lack rep sequences, these must be supplied exogenously, thereby complicating any gene therapy applications using rAAV vectors. On the other hand, infection of a cell with a virus containing a rAAV vector, in the absence of an exogenous source of Rep proteins, will result in limited amplification of the rAAV genome and, consequently, low levels of expression of the heterologous sequence.

Because there can be difficulties in obtaining sufficient levels of expression of heterologous sequences from rAAV vectors and viruses containing such vectors, improvements that increase the efficiency of expression are desirable.

The disclosures of all publications and patents cited herein are hereby incorporated by reference in their entirety.

SUMMARY OF THE INVENTION

The invention provides compositions and methods for improved expression of a heterologous (i.e., non-viral) sequence by a recombinant viral vector, such as adeno-associated virus (rAAV) vector and by recombinant viruses comprising such a vector.

Accordingly, in one aspect, the invention provides a recombinant viral vector comprising a single-stranded heterologous nucleotide sequence comprising a region (one or more regions) which form intrastrand base pairs such that expression of a sequence of interest (such as a heterologous sequence) in the vector is enhanced compared to a vector that lacks sufficient intrastrand base pairing to enhance expression. In some embodiments, sequences in the coding region(s) forms intrastrand base pairs. In other embodiments, the coding region(s) forms intrastrand base pairs. In some embodiments, the recombinant viral vectors are capable of being packaged into a corresponding virus particle.

In some aspects, the viral vector is a parvovirus vector, comprising one or more intverted terminal repeat (ITR) sequences flanking said heterologous sequence.

In another aspect, the invention provides an rAAV vector comprising a single-stranded polynucleotide, with a 5' terminus and a 3' terminus, which contains a heterologous sequence flanked at one or both ends by an AAV inverted terminal repeat (ITR), said heterologous sequence containing one or more regions capable of intrastrand base-pairing (i.e., which form intrastrand base pairs). In preferred embodiments, sequences in the coding region form intrastrand base pairs. In preferred embodiments, the rAAV vectors of the invention are capable of being packaged in an AAV virus particle.

In some embodiments, the heterologous sequence forms base pairs essentially along its entire length, thus analogous to an AAV replicative form (RF). In such embodiments, the sequence complexity of the heterologous sequence is about one half of the length of the heterologous sequence. In some embodiments, the polynucleotide of the rAAV contains an additional, internal ITR (i.e., a non-terminal ITR), preferably approximately in the center of the single strand.

Host cells and virus particles comprising the recombinant viral vectors of the invention are also provided. In another aspect, libraries of recombinant viral vectors described herein are provided.

In another aspect, the invention includes methods for producing parvovirus particles, such as AAV virus particles, containing the recombinant parvovirus (including rAAV) vectors described herein. These methods include the use of a single-stranded parvovirus vector (for example, rAAV) wherein the length of the vector is approximately half the length of a native parvovirus (for example, AAV) genome and wherein the vector comprises a heterologous nucleotide sequence and one or more inverted terminal repeat (ITR) sequences flanking said heterologous sequence. The vector is introduced into a host cell which provides rep function, cap function and, when necessary, helper functions; and the infected host cell is incubated under conditions conducive to viral replication and encapsidation. Recombinant viral vectors (i.e., populations of recombinant viral vectors) produced according to this method, as well as viruses comprising such vectors (i.e., populations of viruses comprising such vectors), are also provided by the invention.

In another aspect, the invention includes methods for introduction of a heterologous sequence (such as a gene of interest) into a host cell using the vectors described herein and methods for expression of a heterologous sequence (such as a gene product of interest) in a host cell, such as a mammalian cells, using the vectors described herein. The methods comprise contacting a recombiant viral vector of the invention (such as a recombinant parovirus vector, for example an rAAV vector) containing a sequence or gene of interest or a recombinant virus particle (such as an rAAV particle) containing such a vector with a host cell under conditions that allow uptake of the vector(s) (which is exogenous polynucleotide), whereby the recombinant viral vector is transfected into the host cell. In the case of expression, a coding region or sequence from the heterologous sequence is transcribed and/or translated.

In addition, the invention provides methods for screening, or identifying a phenotype associated with expression of a coding region in a recombinant viral vector, such as a recombinant parvovirus vector (such as rAAV), of the invention. Such methods will be useful, for instance, in target identification and target validation techniques. These methods entail subjecting a cell (or population of cells) containing a recombinant viral vector(s) described herein to conditions favorable to expression, and comparing the phenotype of this cell(s) to a phenotype of a cell(s) not containing such a recombinant vector, wherein a phenotypic difference indicates a phenotype associated with expression of the coding region(s) of the recombinant viral vector(s). In some embodiments, these methods include the step of introducing the recombinant viral vector(s) of interest.

BRIEF DESCRIPTION OF THE DRAWINGS

FIG. 2 is a schematic diagram of the conversion of an incoming single-stranded AAV genome to a duplex replicative form (RF). In the case of a native AAV genome, formation of the RF allows expression of the rep and cap genes; in the case of a rAAV vector, formation of the RF allows expression of a transgene (i.e., the gene contained in the vector cassette).

FIG. 3 is a schematic diagram showing a model for the replication of AAV. Either a plus strand (left side of figure) or a minus strand (right side of figure) is first converted to a duplex RF. A second round of replication generates a head-to-head or tail-to-tail concatemer, wherein "head" is arbitrarily defined as the left end or (5' end of the plus strand) and "tail" is arbitrarily defined as the right end (or 5' end of the minus strand).

FIG. 4 is a schematic diagram of AAV DI (defective interfering) genomes. The AAV genome is represented in the upper two molecules in its duplex form either with both ends open (resolved) or with one end closed as in the RF. The lower two molecules illustrate the consequence of introducing a deletion between two sites δ and δ'. If the region between δ and δ' is approximately 50% or more of the AAV genome, then the lower-most depicted molecule can be packaged directly into an AAV capsid. Adapted from Carter (1983) In "The Parvoviruses" (K. I. Bems, ed.) Plenum Press, New York, pp. 209–258.

FIGS. 5A–5E illustrate the construction of a half-size AAV-GFP vector.

FIG. 7A shows electrophoresis under alkaline conditions. Lane 1 shows analysis of a DNA fragment containing a half-size vector genome isolated from plasmid pAAVGFP (0.5). Lane 2 shows DNA isolated from half-size vector particles. Lane 3 shows analysis of a DNA fragment containing a full-size vector genome isolated from plasmid pAAVGFP(Sal). Lane 4 shows DNA isolated from full-size vector particles.

FIG. 7B shows electrophoresis under neutral conditions. Lane 1 shows analysis of a DNA fragment containing a half-size vector genome isolated from plasmid pAAVGFP (0.5). Lane 2 shows analysis of a DNA fragment containing a half-size vector genome isolated from plasmid pAAVGFP (0.5) that was denatured prior to loading on the gel. Lane 3 shows analysis of DNA isolated from half-size vector particles. Lane 4 shows DNA isolated from half-size vector particles that was denatured prior to loading on the gel. Lane 5 shows analysis of a DNA fragment containing a full-size vector genome isolated from plasmid pAAVGFP(Sal). Lane 6 shows analysis of a DNA fragment containing a full-size vector genome isolated from plasmid pAAVGFP(Sal) that was denatured prior to loading on the gel. Lane 7 shows DNA isolated from full-size vector particles. Lane 8 shows DNA isolated from full-size vector particles that was denatured prior to loading on the gel.

FIG. 8A shows electrophoresis under neutral conditions. Lane 1 shows analysis of a DNA fragment containing a half-size vector genome isolated from plasmid pAAVGFP (0.5). Lane 2 shows DNA isolated from half-size vector particles. Lane 3 shows vector DNA from adenovirus-infected HeLa cells isolated 6 hours after infection with half-size vector. Lane 4 shows vector DNA from HeLa cells isolated 6 hours after infection with half-size vector. Lane 5 shows vector DNA from HeLa cells isolated 24 hours after infection with half-size vector. Lane 6 shows vector DNA from HeLa cells isolated 48 hours after infection with half-size vector. Lane 7 shows vector DNA from HeLa cells isolated 72 hours after infection with half-size vector. Lane 8 shows analysis of a DNA fragment containing a full-size vector genome isolated from pAAVGFP(Sal). Lane 9 shows DNA isolated from full-size vector particles. Lane 10 shows vector DNA from adenovirus-infected HeLa cells isolated 6 hours after infection with full-size vector. Lane 11 shows vector DNA from HeLa cells isolated 6 hours after infection with full-size vector. Lane 12 shows vector DNA from HeLa cells isolated 24 hours after infection with full-size vector. Lane 13 shows vector DNA from HeLa cells isolated 48 hours after infection with full-size vector. Lane 14 shows vector DNA from HeLa cells isolated 72 hours after infection with full-size vector.

FIG. 8B shows electrophoresis under alkaline conditions. Lane designations are the same as in FIG. 8A. Molecular weight values, determined by parallel analysis of markers, are shown to the left.

FIGS. 9A–B are half-tone reproductions of agarose gel-electrophoresis analysis of vector DNA genomes from particles fractionated in CsCl gradients. FIG. 9A shows electrophoresis under neutral conditions. FIG. 9B shows electrophoresis under alkaline conditions.

Figure 1:
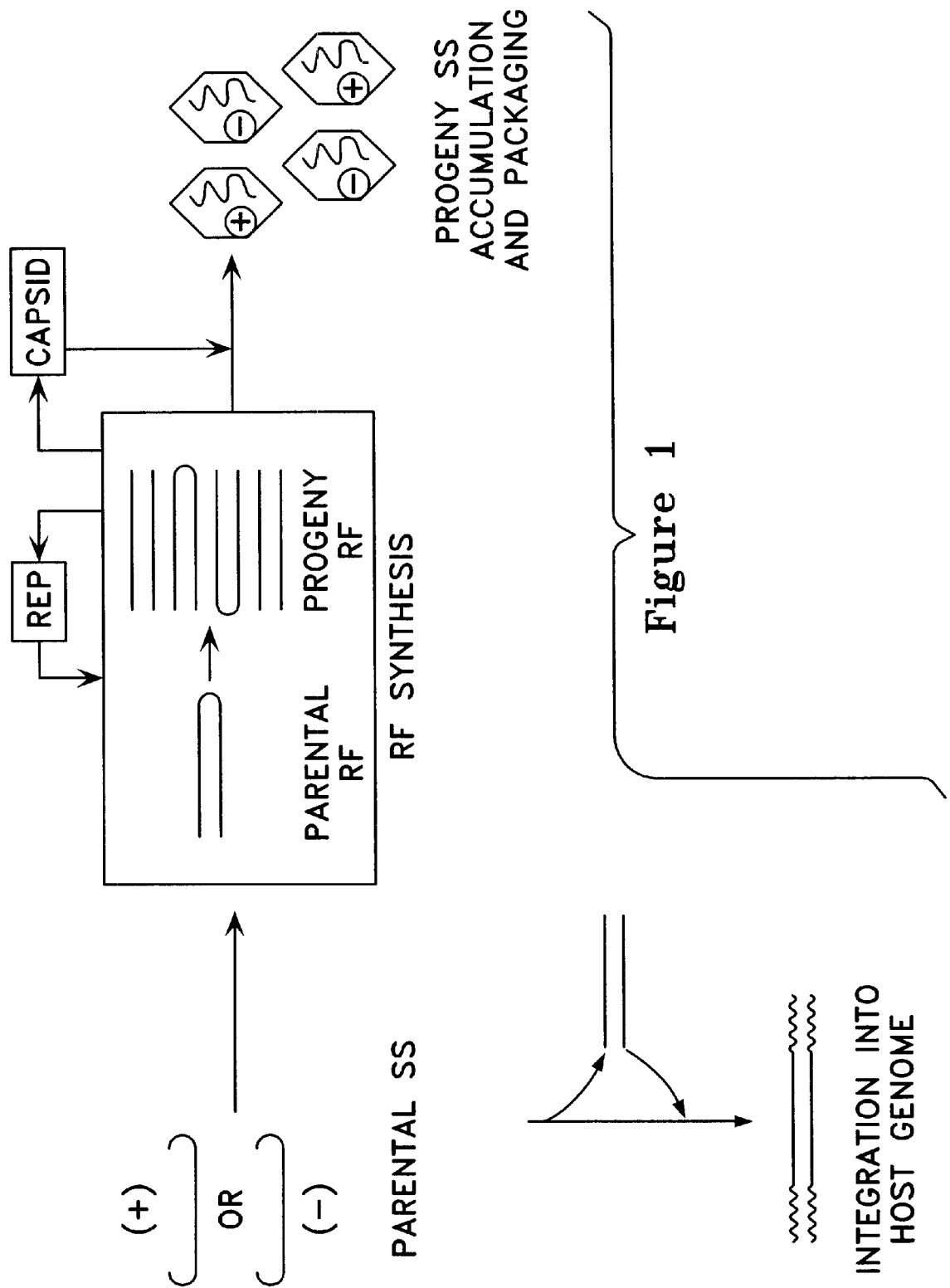
FIG. 1 is a schematic diagram of the AAV life cycle.

Lane designations are the same for both FIGS. 9A and 9B. Lanes 1–5 show analysis of vector genomes from half-size vector particles. Lane 1 shows analysis of particles banding at a density of 1.388 g/ml. Lane 2 shows analysis of particles banding at a density of 1.379 g/ml. Lane 3 shows analysis of particles banding at a density of 1.375 g/ml. Lane 4 shows analysis of particles banding at a density of 1.371 g/ml. Lane 5 shows analysis of particles banding at a density of 1.362 g/ml. Lanes 6–10 show analysis of vector genomes from full-size vector particles. Lane 6 shows analysis of particles banding at a density of 1.394 g/ml. Lane 7 shows analysis of particles banding at a density of 1.387 g/ml. Lane 8 shows analysis of particles banding at a density of 1.381 g/ml. Lane 9 shows analysis of particles banding at a density of 1.377 g/ml. Lane 10 shows analysis of particles banding at a density of 1.372 g/ml. Molecular weight values, determined by parallel analysis of markers, are shown to the left.

FIG. 10 depicts the amino acid sequence of a TNFR:Fc fusion polypeptide from U.S. Pat. No. 5,605,690.

MODES FOR CARRYING OUT THE INVENTION

We have discovered that the capability of a recombinant parvovirus vector to form intrastrand base-pairs contributes to increased levels and/or rate of expression of a heterologous sequence contained in such a vector. rAAV vectors which contained two copies of the green fluorescent protein (GFP) in opposite orientation, and were accordingly able to form a double-stranded molecule due to intrastrand basepairing, displayed significantly higher expression levels (as indicated by percentage of cells expressing reporter gene) in 293 and HeLa cells compared to another vector which was not able to form intrastrand basepairing of the GFP gene. The results observed in HeLa cells are particularly striking, as these cells are known to be inefficient in expression of rAAV vectors. The property of intrastrand basepairing is particularly advantageous in contexts in which it is desirable to obtain more efficient expression of a heterologous sequence, such as in certain gene therapy applications and in genomics screening. Cell types that were traditionally considered impermissive in the sense of inefficient expression (whether due to time course and/or levels of expression) of parvovirus vectors are now practical, useable, hosts.

Without wishing to be bound by theory, the enhanced level and/or rate of expression by the rAAV vectors of the invention may be due to their facility for forming a double-stranded structure. Because the native AAV genome exists as a single-stranded DNA molecule within the virion, expression of a heterologous sequence in an rAAV vector depends upon the formation of a double-stranded replicative form, since transcription requires a double-stranded template. Consequently, conversion of a recombinant AAV vector genome to a double-stranded replicative form (a process also known as "metabolic activation" of the vector) is a critical step in the expression of a heterologous sequence. If an incoming vector genome is either in double-stranded form or is in a form from which it can rapidly adopt a double-stranded conformation, providing transcriptional templates more efficiently and/or earlier during the infective cycle, expression of an inserted sequence is enhanced, as compared to other rAAV vectors. Stated differently, the genome of a metabolically activated rAAV vector will become double-stranded with zero-order kinetics, either within a virus particle or within an infected cell. Thus, for the metabolically activated rAAV vectors of the invention, formation of a base-paired structure is not a critical and/or rate-limiting step in expression of a heterologous sequence or gene of interest.

Thus, the invention provides rAAV vectors capable of forming intrastrand base-pairing of heterologous sequences, as well as compositions and host cells comprising these vectors. The invention also provides methods using these vectors, such as for transfection, transduction, expression, and genomics screening.

As noted above, expression of a heterologous sequence, such as a transgene, from a recombinant parvovirus vector, such as an rAAV vector, is dependent on a number of steps beginning with entry into the host cell, conversion of the single strand to a double-stranded form, and transcription and translation of the heterologous sequence. This process occurs in cells that are phenotypically classified in the art as permissive. As is generally known by one skilled in the art, the terms transduction, transcription, translation, and pemissivity are molecularly and phenotypically distinguishable events that all experimentally can be (and in various publications have been) measured by expression of the transgene according to methods known to one skilled in the art and described herein. The invention described herein relates to recombinant viral vectors (for example, rAAV vectors) which exhibit increased efficiency of expression of a het-erolgous sequence and thus may be referred by one skilled in the art as improving transduction, rendering cells permissive, and/or increasing the rates of transcription or translation.

General Techniques

The practice of the present invention employs, unless otherwise indicated, conventional techniques in virology, biochemistry, molecular biology, microbiology, genetics, recombinant DNA, and related fields as are within the skill of the art. These techniques are fully explained in the literature. See, for example, Maniatis, Fritsch & Sambrook, *Molecular Cloning: A Laboratory Manual*, Cold Spring Harbor Laboratory Press (1982); Sambrook, Fritsch & Maniatis, *Molecular Cloning: A Laboratory Manual*, Second Edition, Cold Spring Harbor Laboratory Press (1989); Ausubel, et al., *Current Protocols in Molecular Biology*, John Wiley & Sons (1987 and annual updates); and related references.

Definitions

As used herein, the singular form "a", "an" and "the" includes plural references unless indicated otherwise. For example, a polynucleotide that contains "a" region that forms intrastrand base pairing can include one or more such regions.

"Recombinant" refers to a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

A "vector," as used herein, refers to a recombinant plasmid or virus that comprises a polynucleotide to be delivered into a host cell, either in vitro or in vivo. The polynucleotide to be delivered, sometimes referred to as a "heterologous sequence," "target polynucleotide," "transgene," or "gene of interest" can comprise a sequence of interest in gene therapy (such as a gene encoding a protein or RNA transcript, such as an antisense transcript or a ribozyme, of therapeutic interest) and/or a selectable or detectable marker.

A "recombinant viral vector" refers to a recombinant polynucleotide vector comprising one or more heterologous sequences (i.e., polynucleotide sequence not of viral origin). In the case of recombinant parvovirus vectors, the recombinant polynucleotide is flanked by at least one, preferably two, inverted terminal repeat sequences (ITRs).

A "recombinant AAV vector (rAAV vector)" refers to a polynucleotide vector comprising one or more heterologous sequences (i.e., polynucleotide sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g. in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV can be in any of a number of forms, including, but not limited to, plasmids, linear artificial chromosomes, complexed with lips, encapsulated within liposomes, and, most preferable, encapsidated in a viral particle, particularly AAV.

An rAAV vector can be packaged into an AAV virus particle to generate a "recombinant adeno-associated virus" (rAAV). The maximum size vector that can be packaged to yield an infectious viral particle is approximately 5.2 kb.

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector, is a heterologous nucleotide sequence with respect to the vector. For purposes of this invention, "heterologous" means heterologous with respect to a virus which is the basis of a recombinant viral vector. Accordingly, and as an example, an rAAV vector of the invention can be used to introduce and/or express a mammalian, and thus "heterologous" sequence, into a mammalian cell.

A "region" of a polynucleotide is a sequence of contiguous nucleotides. A region can be at least about any of the following: 5, 10, 15, 20, 25, 30, 35, 40, 45, 50, 60, 75, 85, 100, 110, 120, 130, 145, 150, 160, 175, 200, 250, 300, 350, 400, 450, 500 or more contiguous nucleotides.

A "coding region" of a polynucleotide (in this invention, a "coding region" of a heterologous sequence) is a sequence of contiguous nucleotides which gives rise in a host cell to a transcription and/or translation product. For example, a "coding region" may give rise to an RNA molecule such as an anti-sense transcript, ribozyme. As another non-limiting example, a coding region may give rise to a polypeptide. It is understood that the "coding region" may give rise to all or a portion of a transcription or translation product, as well as variants and other modified forms. The desired transcription and/or translation product may or may not exhibit a function (i.e., it may or may not exhibit a detectable or measurable phenotype when present in a host cell). This is especially a consideration in genomics screening applications, in which candidate sequences are tested for function. A coding region can be at least about any of the following: 5, 10, 15, 20, 25, 30, 35, 40, 45, 50, 60, 75, 85, 100, 110, 120, 130, 145, 150, 160, 175, 200, 250, 300, 350, 400, 450, 500 or more contiguous nucleotides.

A "region (or sequence) which forms intrastrand base pairs" (including a coding region which forms intrastrand base pairs) is a region (such as a coding region) which is complementary in sequence to another region in the same strand, and is thus capable of forming base pairs with the complementary sequence, i.e., is self-annealing. Base-pairing interactions proceed according to well-known and art-recognized molecular properties of nucleotide bases, such that adenine base-pairs with thymine or uracil, and guanine base-pairs with cytosine. Thus, adenine is complementary to both thymine and uracil, and vice versa; similarly, guanine is complementary to cytosine and vice versa. If a first polynucleotide sequence is complementary along its entire length with a second polynucleotide sequence, the two sequences are said to be perfectly complementary, perfectly matched, or fully complementary to each other. If a majority of bases in a first polynucleotide sequence are complementary to those in a second polynucleotide sequence, but one or more bases are noncomplementary, the two polynucleotide sequences are said to be substantially complementary to each other if their degree of complementarity is sufficient to allow duplex formation. It is understood that, for purposes of this invention, a recombinant viral vector containing a sequence or region that forms intrastrand base pairs exhibits enhanced expression when compared to an otherwise similar (or identical) vector except for the degree of intrastrand base pairing. Thus, the extent of intrastrand base pairing need not be 100% of the sequence but may be at least about any of the following: 25%, 40%, 50%, 60%, 65%, 70%, 75%, 80%, 85%, 88%, 90%, 92%, 95%, 98%, 99%. In some aspects, intrastrand base pairing is sufficient to allow transcription without previous DNA replication of the strand. Generally, for purposes of this invention, intrastrand base pairs will exist in a host cell during expression and/or replication of the coding region of interest. Intrastrand base pairs can but will not necessarily occur before a recombinant viral vector of the invention is introduced into a host cell, such as packaged into an rAAV particle.

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity, allowing intrastrand.base-pairing to occur within this portion of the ITR.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

"Helper function" refers to an activity that is for required replication and/or packaging of a parvovirus but is not encoded within that parvovirus. Helper function can be provided by a helper virus. Helper functions are also believed to stimulate transcription of some AAV promoters, including p5, and may enhance processivity of replication in cells in which helper functions are expressed.

A "promoter," as used herein, refers to a nucleotide sequence that directs the transcription of a gene or coding sequence to which it is operably linked.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the transcriptional regulatory sequence or promoter facilitates some aspect of the transcription of the coding sequence. Aspects of the transcription process include, but are not limited to, initiation, elongation, attenuation and termination. An operably linked transcriptional regulatory sequence is generally joined in cis with the coding sequence, but it is not necessarily directly adjacent to it.

A "replicon" refers to a polynucleotide comprising an origin of replication which allows for replication of the polynucleotide in an appropriate host cell. Examples of replicons include viruses, episomes (including plasmids), as well as chromosomes (such as nuclear or mitochondrial chromosomes).

A "replication origin" is a nucleotide sequence involved in one or more aspects of initiation of AAV DNA replication, such as, for example, replication initiation, unwinding of the DNA duplex, primer formation, and/or template-directed synthesis of a complementary strand. The AAV replication origin is located within the AAV inverted terminal repeat (ITR) sequence and facilitates replication of sequences to which it is operably linked. In the practice of the invention, an AAV origin can be substituted with an ori-like sequence, as disclosed in co-owned PCT WO 99/20779.

"Packaging" refers to a series of subcellular events that results in the assembly and encapsidation of a viral vector, such as an rAAV vector. Thus, when a suitable vector is introduced into a packaging cell line under appropriate conditions, it can be assembled into a viral particle.

"Transduction" is the introduction of an exogenous gene into a cell by viral infection, wherein the exogenous gene is part of a recombinant viral genome. "rep and cap genes" are genes encoding replication and encapsidation proteins, respectively. "AAV rep and cap genes" are AAV genes encoding replication and encapidation proteins. AAV rep and cap proteins have been found in all AAV serotypes examined, and are described herein and in the references cited. In wild-type AAV, the rep and cap genes are generally found adjacent to each other in the viral genome (i.e. they are "coupled" together as adjoining or overlapping transcriptional units), and they are generally conserved among AAV serotypes. AAV rep and cap genes may be individually and collectively referred to as "AAV packaging genes." AAV packaging genes that have been modified by deletion or point mutation, or which have been subdivided into components which can be rejoined by recombination (e.g. as described in co-owned PCT WO 98/27204, the disclosure of which is hereby incorporated by reference), may also be used in the present invention. AAV packaging genes can also be operably linked to other transcriptional regulatory sequences, including promoters, enhancers and polyadenylation ("polyA") sequences (which additional transcriptional regulatory sequences can also be heterologous). An "AAV packaging cassette" is a recombinant construct which includes one or more AAV packaging genes.

A "host cell" is a cell which has been or can be a recipient for a vector(s) of this invention and the progeny thereof. The progeny may not be necessarily be completely identical (in morphology or in genomic of total DNA complement) to the original parent cell due to-natural, accidental, or deliberate mutation. Host cells are preferably eukaryotic cells, preferably mammalian cells, most preferably human cells.

The terms "therapeutic gene", "target polynucleotide", "transgene", "gene of interest", "heterologous sequence" and the like generally refer to a sequence or sequences to be transferred using a vector. Preferably, such sequences are located within a recombinant parvovirus vector, more preferably an rAAV vector (which vector is flanked by at least one, preferably two ITR regions and thus can be replicated and encapsidated into rAAV particles). Target polynucleotides can be used in this invention to generate recombinant parvovirus vectors (preferably rAAV) for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; (vi) polynucleotides for cancer therapy, such as E1A tumor suppressor genes or p53 tumor suppressor genes for the treatment of various cancers and (vii) polynucleotides that encode antigens or antibodies. To effect expression of the transgene in a recipient host cell, it is preferably operably linked to a promoter or other such transcriptional regulatory sequence, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The recombinant vector can also contain a selectable marker.

A "gene product" is a product encoded by a nucleic acid sequence, preferably a DNA sequence, and can be RNA or protein. Examples of RNA gene products include mRNA, rRNA, tRNA, structural RNA, catalytic RNA and ribozymes. Examples of protein gene products, encoded by way of a mRNA intermediate, include structural proteins and enzymes.

"Expression" includes transcription and/or translation. Methods of detecting transcription, such as Northern analysis, and translation, such as Western analysis or ELISA, are well known in the art. These methods also permit measuring differing levels of transcription and/or translation, whether that difference is between or among different vectors, different times, different host cells, etc.

"Polynucleotide" refers to a polymeric form of nucleotides of any length. Polynucleotides can comprise ribonucleotides, deoxyribonucleotides, analogs thereof, or any combination of the aforementioned. The term includes single-, double- and triple-stranded nucleic acids, as well as higher order structures, such as quartets. It also includes modified polynucleotides such as methylated or capped polynucleotides, and polynucleotide analogues, such as polyamide (peptide) nucleic acids. Polynucleotides can be linear, branched or circular molecules. A linear polynucleotide has two termini; in the case of a single-stranded polynucleotide, these can be characterized as a 5' terminus and a 3' terminus.

The term "sequence complexity" or "complexity" refers to the total amount of unique sequence present in a polynucleotide. For example, a non-repeated nucleotide sequence with a length of 500 nucleotides has a complexity of 500 nucleotides, while a sequence having a length of 500 nucleotides that is composed of two copies of an identical (or nearly identical) 250-nucleotide sequence has a complexity of 250 nucleotides. Sequence complexity can be determined by measurement of the rate of reassociation between two complementary polynucleotides, with higher complexity correlating with slower rates. See, for example, Britten et al. (1985) in "Nucleic Acid Hybridisation: A Practical Approach" (ed. B. D. Hames & S. J. Higgins) IRL Press, Oxford, Chapter 1, pp. 3–15 and references cited therein. Sequence complexity can also be determined directly by DNA sequencing.

A "library" is a population of vectors, wherein individual vectors contain different heterologous sequences, and the heterologous sequences reflect the nucleic acid population of a particular cell, tissue, or developmental stage, for example. For example, a "cDNA library" is a population of vectors containing a plurality of distinct cDNA inserts, wherein the cDNA inserts are derived from a mRNA population. A "genomic library" is a population of vectors having a plurality of distinct inserts, in which each insert represents a portion of the genome of a cell or organism.

Conditions that "allow" an event to occur, such as uptake of an exogenous polynucleotide, such as a recombinant viral vector, into a cell, such as a mammalian cell, or infection by a virus, are conditions that do not prevent such events from occurring. Thus, these conditions permit, enhance, facilitate, and/or are conducive to the event, such as entry of the exogenous polynucleotide into the cell. Such conditions, known in the art and described herein, depend upon the nature of the cell as well as the exogenous polynucleotide (i.e., whether introduced as a naked, complexed, or packaged vector). These conditions also depend on what event is desired, such as expression or infection.

A "phenotype" is a detectable cellular and/or molecular event or condition which arises from the genetic composition of a cell or organism.

An "individual" is a vertebrate, preferably a mammal, and includes, but is not limited to, domestic animals, farm animals, rodents, primates, and humans.

An "effective amount" is an amount sufficient to effect beneficial or desired results, including clinical results. An effective amount can be administered in one or more administrations. In terms of a disease state, an effective amount is an amount sufficient to ameliorate, stabilize, or delay development of a disease.

Recombinant Viral Vectors of the Invention and Compositions Comprising the Recombinant Viral Vectors The invention provides recombinant viral vectors which comprise a single-stranded heterologous nucleotide sequence in which one or more regions form intrastrand base pairs. The virus which forms the basis of the vector may be any virus, and is preferably a virus which normally (i.e., as found in nature) contains one or more single stranded regions, and more preferably is normally single-stranded.

In preferred embodiments, the virus vector is a parvovirus vector. Examples of parvovirus are MVM, MVH1, MMV (mice minute virus), canine parvovirus, feline parvovirus, feline panleukopenia, HB parvovirus, CMV (canine minute virus), adeno-associated virus (AAV), densovirus. A particularly preferred embodiment, exemplified herein, is AAV. However, it is understood that many principles as described for AAV apply to other parvoviruses. Further, techniques for making and using viral vectors are described in the art.

In some embodiments, the invention provides a single-stranded polynucleotide rAAV vectors in which one or more regions of heterologous sequence, preferably coding sequence, form intrastrand base pairs. The rAAV vectors of the invention contain a 5' and 3' terminus (i.e., are not circular) as well as an ITR(s) which flanks one or both ends.

The region(s) of intrastrand complementarity (i.e., the region(s) which form intrastrand base pairs) in the recombinant viral vector are positionally and/or quantitatively sufficient to enhance expression of a nucleotide sequence of interest contained within the vector as compared to a vector that is structurally analogous except for the position and/or quantity of base pairing, such that the analogous vector lacks sufficient intrastrand complementarity to enhance expression of the nucleotide sequence of interest. In preferred embodiments, the region(s) of intrastrand base pairing are within the coding region(s), i.e., the intrastrand base pairing occurs within a nucleotide sequence that is to be expressed. In other preferred embodiments, the entire coding region(s) is base paired.

The regions of intrastrand complementarity may be anywhere along the heterologous sequence and may be any of a number of sizes, in terms of contiguous nucleotides. Further, it is understood that the region or sequence of intrastrand base pairing may or may not be within a coding region of a heterolgous sequence. In some embodiments, a region(s) is adjacent to, or, alternatively, near to, a (5' or 3') terminus. In other embodiments, a region(s) is adjacent to, or near to, the center of the rAAV molecule. A region can be at least about any of the following: 5, 10, 15, 20, 25, 30, 35, 40, 45, 50, 60, 75, 85, 100, 110, 120, 130, 145, 150, 160, 175, 200, 250, 300, 350, 400, 450, 500 or more contiguous nucleotides. In some embodiments, the total amount of sequence that forms intrastrand base pairs (which could be in one or more regions) is greater than about 125 nucleotides, greater than about 250 nucleotides, greater than about 500 nucleotides, and/or greater than about 1,000 nucleotides.

If a heterologous sequence contains more than one such region, the regions may be separated by several to several hundred nucleotides. Most preferably, the region should encompass the sequence for which expression (i.e., transcription and/or translation) is desired. For example, an rAAV vector may contain two sequences for anti-sense expression, or two small genes, either contiguous (i.e., no intervening nucleotides) or separated by non-coding nucleotides. The vector also contains complementary sequences (in opposite orientation, to allow base pairing) for the two "coding" sequences.

In one embodiment, the recombinant viral vectors of the invention have sequence complexity that is approximately one half its length, with the sequences arranged such that one portion of the molecule comprises an inverted complement of another portion. Under these circumstances, a vector is able to form a "snapback" molecule which is double-stranded along most or all of its length, thus analogous to the RF produced during AAV infection. Preferably, this "half-complexity" vector is an rAAV vector.

In other embodiments, a recombinant parvovirus vector, preferably an rAAV vector, further comprises an internal ITR (i.e., an ITR that is flanked on both sides by heterologous sequences), which is other than the ITR(s) flanking the heterologous sequence. This internal ITR preferably divides the heterologous sequence, such that intrastrand base pairing occurs between region(s) on either side of the internal ITR. Most preferably, essentially all of the heterologous sequence on either side of the ITR are engaged in intrastrand base pairing. Examples 4–7 illustrate such a vector.

In general, the recombinant viral vectors of the invention are capable of being packaged into a viral particle, especially the type viral particle which is the basis of the vector. For example, a recombinant parvovirus vector of the invention is capable of being packaged into a parvovirus particle. In preferred embodiments, rAAV vectors of the invention are capable of being packaged into an AAV particle; accordingly, their size can range up to about 5.2 kb and/or the packaging limit of the AAV being used. It is understood, however, that a recombinant viral vector of the invention may be, and often will be, smaller than a packaging limit. In the case of an rAAV vector of the invention, its length may be less than about any of the following: 5.5, 5.2, 5.0, 4.8, 4.5, 4.0, 3.8, 3.5, 3.0, 2.8, 2.5, 2.0, 1.8, 1.5, 1.0, 0.8, 0.6, 0.5, 0.4, 0.3, 0.2 kilobases.

In another embodiment, recombinant virus particles comprising a recombinant viral vector of the invention are provided. In one embodiment, the invention provides recombinant AAV particles comprising an rAAV vector of the invention. Methods for making virus particles (such as parvovirus particles) are known in the art, and methods for making rAAV are provided herein as well as in the art. With respect to AAV, any serotype is suitable, since the various serotypes are functionally and structurally related, even at the genetic level (see; e.g., Blacklow, pp. 165–174 of "Parvoviruses and Human Disease" J. R. Pattison, ed. (1988); and Rose, Comprehensive Virology 3:1, 1974). The AAV2 serotype was used in some of the illustrations of the present invention that are set forth in the Examples. However, it is fully expected that the same principles derived from analysis of AAV2 will be applicable to other AAV serotypes, since it is known that the various serotypes are quite closely related, both functionally and structurally, even at the genetic level. See, e.g., Blacklow (1988) *Parvoviruses and Human Disease*, J. R. Pattison (ed.) pp. 165–174; and Rose (1974) *Comprehensive Virology* 3:1–61. All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed. For a general review of AAV biology and genetics, see, e.g., Carter, "Handbook of Parvoviruses", Vol. I, pp. 169–228 (1989), and Berns, "Virology", pp. 1743–1764, Raven Press, (1 990). General principles of rAAV vector construction are known in the art. See, e.g., Carter, 1992, *Current Opinion in Biotechnology*, 3:533–539; and Muzyczka, 1992, *Curr. Top. Microbiol. Immunol.*, 158:97–129.

With respect to the vectors, virus particles containing the vectors, compositions, and methods using these aforementioned moieties, populations of such vectors (and/or viruses) may be made and used. For example, as discussed below, some methods of making such viral vectors may lead to a population of vectors which contain vectors which have intrastrand base-pairing. During the process of replication (in making these vectors), some single stranded genomes may become nicked and retain their duplex structure. These duplex molecules are considered functionally equivalent to the intrastrand duplex molecules described herein, and accordingly this invention encompasses such populations and other closely related moieties (as well as methods using these populations and closely related moieties), such as "nicked" vectors.

Accordingly, the invention provides recombinant viral vectors in which a heterologous region forms a duplex without host cell DNA replication. The duplex formation is such that expression of a sequence of interest is enhanced when compared to a structurally analogous vector which lacks sufficient duplex formation to enhance expression of the sequence of interest.

Compositions

In other embodiments, the invention provides compositions comprising any of the recombinant viral vectors (and/or recombinant virus particles described herein, such as rAAV vectors (and/or rAAV virus particles comprising the rAAV vectors). These compositions are useful for, inter alia, administration to an individual for the purpose of gene delivery as well as contacting with suitable host cells for phenotypic screening.

Generally, these compositions contain components which facilitate their use, such as pharmaceutical excipients and/or appropriate buffers. For pharmaceutical uses, the compositions generally comprise an effective amount of a recombinant virus vector, such as an rAAV vector, preferably in a pharmaceutically acceptable excipient. As is well known in the art, pharmaceutically acceptable excipients are relatively inert substances that facilitate administration of a pharmacologically effective substance and can be supplied as liquid solutions or suspension, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, and buffers. Excipients as well as formulations for parenteral and nonparenteral drug delivery are set forth in *Remington's Pharmaceutical Sciences* 19th Ed. Mack Publishing (1995). The pharmaceutical compositions also include lyophilized and/or reconsituted forms of the recombinant viral vectors of the invention, and can be used in the in vitro as well as in vivo setting.

Generally, these pharmaceutical compositions are formulated for administration by injection (e.g., intra-articularly, intravenously, intramuscularly, etc.). Accordingly, these compositions are preferably combined with pharmaceutically acceptable vehicles such as saline, Ringer's balanced salt solution (pH 7.4), dextrose solution, and the like. Although not required, pharmaceutical compositions may optionally be supplied in unit dosage form suitable for administration of a precise amount.

For in vitro introduction to host cells, such as in screening applications, the compositions contain agents such as salts and buffers, which promote viral infection and/or uptake of the viral vector(s) by the cells. Such agents are well-known in the art.

The invention also includes any of the above vectors (or compositions comprising the vectors) for use in treatment (due to expression of a therapeutic gene). The invention further provides use of any of the above vectors (or compositions comprising the vectors) in the manufacture of a medicament for treatment.

Host Cells and Libraries

The invention also provides host cells comprising recombinant viral vectors described herein. In preferred embodiments, the viral vector is an rAAV vector. Among eukaryotic host cells are yeast, insect, avian, plant and mammalian cells. Preferably, the host cells are mammalian, including cell lines and primary cells. For example, host cells include, but are not limited to, HeLa, 293, and primary fetal foreskin fibroblast cells, all of human origin and readily available. These cells result from contact of the vector polynucleotide with a host cell using methods well-known in the art for introducing nucleic acids into cells under conditions which allow uptake of nucleic acid and nonhomologous insertion of exogenous nucleic acid into a genome. Methods and compositions for introducing the recombiment vector(s) into the host cell and for determining whether a host cell contains the vector(s) are discussed herein as exemplified by rAAV vectors and are well known in the art.

Included in these embodiments, and discussed below, are so-called "producer cells" used as a basis for producing packaged rAAV vectors.

Also included are libraries comprising recombinant viral vectors described herein, such as rAAV vectors. It will be apparent to those of skill in the art that a cell population that is exposed to a number of recombinant viral vectors of the invention, i.e., vectors containing various heterologous sequences, under conditions allowing uptake of exogenous DNA, will be composed of a plurality of cells, wherein the majority of the cells will be characterized by each cell having a particular viral vector, compared to the other cells in the population. That is, a library of cells will be generated, in which the majority of cells in the library have a unique coding sequence that is different from the coding in any other, or most other, cell in the library. This library of marked cells will be useful in various types of functional genomics investigations, such as comparison of diseased cells with their normal counterparts, comparisons of cells at different developmental stages, etc.

Production of Recombinant Viral Vectors of the Invention

The recombinant viral vectors of the invention can be produced by any method known in the art such as recombinant and synthetic methods, which are well-described in the art. For parvovirus embodiments, any method is suitable that will generate a single-stranded polynucleotide molecule as described flanked by at least one ITR. As an example, known synthetic techniques can be used to synthesize a double-stranded molecule comprising a sequence of interest flanked by one or more ITR sequences. Such a molecule can be denatured and its constituent single strands can be recovered. Alternatively, single strands can be obtained after cloning such a double-stranded molecule in a filamentous phage cloning vector, such as M13, fl or fd, for example, as is known to those of skill in the art. A purified single-strand will be capable of forming a short hairpin at each of its termini, because of the ITR sequences located there. Extension of the short hairpin by a nucleic acid polymerase in the presence of deoxynucleoside triphosphates will generate a metabolically activated vector.

In another embodiment, a single-stranded polynucleotide comprising a sequence of interest with an ITR at one end is used. Such a polynucleotide can be obtained, for example, by denaturation of a corresponding double-stranded polynucleotide, or by recovery from a filamentous phage cloning vector. Extension of the short hairpin formed by the terminal ITR sequence will generate a double-stranded molecule, covalently closed at one end, with a partial ITR sequence at the covalently closed end. Optionally, a double-stranded ITR sequence can be ligated to the opposite end, by techniques well-known to those of skill in the art.

In another embodiment, recombinant parvovirus vectors of the invention can be produced by constructing a parvovirus vector, such as an rAAV vector, that has a size approximately one-half of a native genome and allowing such a vector to replicate in a host cell. In the case of rAAV, a host cell accordingly provides rep and cap functions as well as helper functions. Upon replication, the half-size genome is copied into a complementary DNA strand that is covalently attached to its template at one end (see FIGS. 1 and 3), forming a structure that will "snap back" into a hairpin duplex. These genome structures, having a single-stranded length comparable to that of a native genome (such as AAV), can be packaged into virus particles under appropriate conditions in a cell which is rendered permissive by expression of helper functions (in the case of AAV) and in which the rep and cap genes are also expressed. These recombinant parvovirus vectors comprise an ITR sequence between the heterologous sequences (i.e., an ITR sequence flanked on both sides by heterologous sequences).

As an example of this production method, a plasmid of approximately one-half the size of a native AAV genome, i.e., about 2,300–2,400 base pairs, is transfected into a producer cell line that, in addition, is either infected with a helper virus or expresses helper functions. A non-limiting example of a producer cell line is the C12 line. C12 is a HeLa cell line containing a rep and cap gene cassette, in which Rep and Cap expression is induced upon infection with adenovirus. When C12 cells (or equivalent cell lines)

are concurrently infected with adenovirus and transfected with a vector plasmid, the vector genome is amplified and encapsidated into AAV particles. For a rAAV genome having a size comparable to a native AAV genome, genomes corresponding to either strand of the vector can be packaged into virus particles.

As described above, the recombinant viral vectors of this invention comprise a heterologous polynucleotide. Since transcription of a heterologous polynucleotide in the vector is generally desired in the intended target cell, it can be operably linked to its own or to a heterologous promoter and/or enhancer, depending for example on the desired level and/or specificity of transcription within the target cell, as is known in the art. Various types of promoters and enhancers are suitable for use in this context. For example, Feldhaus (U.S. patent application Ser. No. 09/171,759, filed Oct. 20, 1998) describes a modified ITR comprising a promoter to regulate expression from an rAAV. Constitutive promoters provide an ongoing level of gene transcription, and are preferred when it is desired that the therapeutic polynucleotide be expressed on an ongoing basis. Inducible or regulatable promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific, that is, they exhibit their activity only in certain cell types, presumably due to gene regulatory elements found uniquely in those cells. Such tissue-specific promoters and enhancers are known in the art. By way of illustration, an example of tissue-specific promoters includes various myosin promoters for expression in muscle. Another example of tissue-specific promoters and enhancers are of regulatory elements for cell and/or tissue types that are in a joint.

Further illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Additional inducible promoters include heavy metal ion inducible promoters (such as the mouse mammary tumor virus (mMTV) promoter or various growth hormone promoters), and the promoters from T7 phage which are active in the presence of T7 RNA polymerase. A large variety of other promoters are known and generally available in the art, and the sequences for many such promoters are available in sequence databases such as the GenBank database.

When translation is also desired in an intended target cell, the heterologous polynucleotide preferably also comprises control elements that facilitate translation (such as a ribosome binding site or "RBS" and a polyadenylation signal). Accordingly, the heterologous polynucleotide will generally comprise at least one coding region operatively linked to a suitable promoter, and can also comprise, for example, an operatively linked enhancer, ribosome binding site and poly-A signal. The heterologous polynucleotide can comprise one encoding region, or more than one encoding region under the control of the same or different promoters. The entire unit, containing a combination of control elements and encoding region, is often referred to as an expression cassette.

A heterologous polynucleotide is integrated by recombinant techniques into or preferably in place of the viral genomic coding region (for example, in place of the AAV rep and cap genes), but, in the case of parvovirus, is generally flanked on either side by ITRs. This means that an ITR appears both upstream and downstream from the coding sequence, either in direct juxtaposition, preferably (although not necessarily) without any intervening sequence of viral origin in order to reduce the likelihood of recombination. In the case of AAV, such recombination might regenerate a replication-competent AAV ("RCA") genome. Recent evidence suggests that a single ITR can be sufficient to carry out the functions normally associated with configurations comprising two ITRs (U.S. Pat. No. 5,478745), and vector constructs with only one ITR can thus be employed in conjunction with the packaging and production methods described herein. The resultant recombinant viral vector is referred to as being "defective" in viral functions when specific viral coding sequences are deleted from the vector.

The recombinant viral vectors are provided in a variety of forms, such as in the form of bacterial plasmids, viral particles, liposomes or any combination thereof. In other embodiments, the recombinant viral vector sequence is provided in the host cells transfected with the viral vector.

The following is a more detailed description of examples and principles of suitable production systems for rAAV vectors (and AAV containing these vectors). It is understood that many of the principles described herein apply to other parvoviruses.

For encapsidation within AAV2 particles, the heterologous polynucleotide will preferably be less than about 5 kb although other serotypes and/or modifications may be employed to allow larger sequences to packaged into the AAV viral particles. Given the relative encapsidation size limits of various AAV genomes, insertion of a large heterologous polynucleotide into the genome necessitates removal of a portion of the AAV genome, in particular, one or more of the packaging genes may be removed. Removal of one or more AAV genes is in any case desirable, to reduce the likelihood of generating RCA. Accordingly, encoding or promoter sequences for rep, cap, or both, are preferably removed, since the functions provided by these genes can be provided in trans.

If the rAAV is to be used in the form of a packaged rAAV particle and a gene therapy use is intended, there are at least three desirable features of an rAAV virus preparation for use in gene transfer. First, it is preferred that the rAAV virus should be generated at titers sufficiently high to transduce an effective proportion of cells in the target tissue. High number of rAAV viral particles are typically required for gene transfer in vivo. For example, some treatments may require in excess of $10^8$ particles. Second, it is preferred that the rAAV virus preparations should be essentially free of replication-competent AAV (i.e., phenotypically wild-type AAV which can be replicated in the presence of helper virus or helper virus functions). Third, it is preferred that the rAAV virus preparation as a whole be essentially free of other viruses (such as a helper virus used in AAV production) as well as helper virus and cellular proteins, and other components such as lipids and carbohydrates, so as to minimize or eliminate any risk of generating an immune response in the context of gene transfer.

If an rAAV vector is to be packaged in an AAV particle, in order to replicate and package the rAAV vector, the missing functions are complemented with a packaging gene, or a plurality thereof, which together encode the necessary functions for the various missing rep and/or cap gene products. The packaging genes or gene cassettes are preferably not flanked by AAV ITRs and preferably do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of the homologous sequences and with their level of shared identity. The level of homology that will pose a concern in a given system can be determined theoretically and confirmed experimentally, as is known in the art. Generally, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al. in U.S. patent application Ser. No. 08/769,728, filed Dec. 18, 1996.

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., U.S. Pat. No. 5,837,484; Burstein et al., WO 98/27207; and Johnson et al., U.S. Pat. No. 5,658,785). The AAV cap gene, providing the encapsidation proteins as described above, can be provided together with an AAV rep gene or separately (see, e.g., the above-referenced applications and patents as well as Allen et al. (WO 96/17947). Other combinations are possible.

As is described in the art, and illustrated in the references cited above and in Examples below, genetic material can be introduced into cells (such as mammalian "producer" cells for the production of rAAV) using any of a variety of means to transform or transduce such cells. By way of illustration, such techniques include, but are not limited to, transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug resistance gene as a selectable marker. Drug resistant cells can then be picked and grown, and then tested for expression of the desired sequence (i.e., a product of the heterologous polynucleotide). Testing for acquisition, localization and/or maintenance of an introduced polynucleotide can be performed using DNA hybridization-based techniques (such as Southern blotting and other procedures as known in the art). Testing for expression can be readily performed by Northern analysis of RNA extracted from the genetically altered cells, or by indirect immunofluorescence for the corresponding gene product. Testing and confirmation of packaging capabilities and efficiencies can be obtained by introducing to the cell the remaining functional components of AAV and a helper virus, to test for production of AAV particles. Where a cell is inheritably altered with a plurality of polynucleotide constructs, it is generally more convenient (though not essential) to introduce them to the cell separately, and validate each step seriatim. References describing such techniques include those cited herein.

In one approach to packaging rAAV vectors in an AAV particle, the rAAV vector sequence (i.e., the sequence flanked by AAV ITRs), and the AAV packaging genes to be provided in trans, are introduced into the host cell in separate bacterial plasmids. Examples of this approach are described in Ratschin et al., 1984, *Mol. Cell. Biol.*, 4:2072; Hermonat et al., 1984, *Proc. Natl. Acad. Sci. USA*, 81:6466; Tratschin et al., 1985, *Mol. Cell. Biol.*, 5:3251; McLaughlin et al., 1988, *J. Virol.*, 62:1963; Lebkowski et al., 1988, *Mol. Cell. Biol.*, 7:349; Samulski et al., 1989, *J. Virol.*, 63:3822–3828; and Flotte et al., 1992, *Am. J. Respir. Cell. Mol. Biol.*, 7:349.

A second approach is to provide either the rAAV vector sequence, or the AAV packaging genes, in the form of an episomal plasmid in a mammalian cell used for AAV replication. See, for example, U.S. Pat. No. 5,173,414.

A third approach is to provide either the rAAV vector sequence or the AAV packaging genes, or both, stably integrated into the genome of the mammalian cell used for replication, as exemplified in Example 2 below.

One exemplary technique of this third approach is outlined in international patent application WO 95/13365 (Targeted Genetics Corporation and Johns Hopkins University) and corresponding U.S. Pat. No. 5,658,776 (by Flotte et al.). This example uses a mammalian cell with at least one intact copy of a stably integrated rAAV vector, wherein the vector comprises an AAV ITR and a transcription promoter operably linked to a target polynucleotide, but wherein the expression of rep is limiting in the cell. In a preferred embodiment, an AAV packaging plasmid comprising the rep gene operably linked to a heterologous promoter is introduced into the cell, and then the cell is incubated under conditions that allow replication and packaging of the rAAV vector sequence into particles.

Another approach is outlined in Trempe et al., U.S. Pat. No. 5,837,484. This example uses a stable mammalian cell line with an AAV rep gene operably linked to a heterologous promoter so as to be capable of expressing functional Rep protein. In various preferred embodiments, the AAV cap gene can be provided stably as well or can be introduced transiently (e.g. on a plasmid). An rAAV vector can also be introduced stably or transiently.

Another approach is outlined in patent application WO 96/17947 (Targeted Genetics Corporation). This example uses a mammalian cell which comprises a stably integrated AAV cap gene, and a stably integrated AAV rep gene operably linked to a helper virus-inducible heterologous promoter. A plasmid comprising the rAAV vector sequence is also introduced into the cells (either stably or transiently). The packaging of rAAV vector into particles is then initiated by introduction of the helper virus.

Methods for achieving high titers of rAAV virus preparations that are substantially free of contaminating virus and/or viral or cellular proteins are outlined by Atkinson et al. in WO 99/11764. Techniques described therein can be employed for the large-scale production of rAAV viral particle preparations.

These various examples address the issue of producing rAAV viral particles at sufficiently high titer, minimizing recombination between rAAV vector and sequences encoding packaging components, reducing or avoiding the potential difficulties associated with the expression of the AAV rep gene in mammalian cell line (since the Rep proteins can not only limit their own expression but can also affect cellular metabolism) and producing rAAV virus preparations that are substantially free of contaminating virus and/or viral or cellular protein.

Packaging of an AAV vector into viral particles relies on the presence of a suitable helper virus for AAV or the provision of helper virus functions. Helper viruses capable of supporting AAV replication are exemplified by adenovirus, but include other viruses such as herpes viruses (including, but not limited to, HSV1, cytomegalovirus and HHV-6) and pox virus (particularly vaccinia). Any such virus may be used.

Frequently, the helper virus will be an adenovirus of a type and subgroup that can infect the intended host cell. Human adenovirus of subgroup C, particularly serotypes 1, 2, 4, 6, and 7, are commonly used. Serotype 5 is generally preferred.

The features and growth patterns of adenovirus are known in the art. See, for example, Horowitz, "Adenoviridae and their replication", pp 771–816 in "Fundamental Virology", Fields et al., eds. The packaged adenovirus genome is a linear DNA molecule, linked through adenovirus ITRs at the left- and right-hand termini through a terminal protein complex to form a circle. Control and encoding regions for early, intermediate, and late components overlap within the genome. Early region genes are implicated in replication of the adenovirus genome, and are grouped depending on their location into the E1, E2, E3, and E4 regions.

Although not essential, in principle it is desirable that the helper virus strain be defective for replication in the subject ultimately to receive the genetic therapy. Thus, any residual helper virus present in an rAAV virus preparation will be replication-incompetent. Adenoviruses from which the E1A or both the E1A and the E3 region have been removed are not infectious for most human cells. They can be replicated in a permissive cell line (e.g., the human 293 cell line) which is capable of complementing the missing activity. Regions of adenovirus that appear to be associated with helper function, as well as regions that do not, have been identified and described in the art (see, e.g., P. Colosi et al., WO97/17458, and references cited therein).

For example, as described in Atkinson et al. (WO 99/11764), a "conditionally-sensitive" helper virus can also be employed to provide helper virus activity. Such a helper virus strain must minimally have the property of being able to support AAV replication in a host cell under at least one set of conditions where it itself does not undergo efficient genomic replication. Where helper virus activity is supplied as intact virus particles, it is also generally necessary that the virus be capable of replication in a host cell under a second set of conditions. The first set of conditions will differ from the second set of conditions by a readily controllable feature, such as the presence or absence of a required cofactor (such as a cation), the presence or absence of an inhibitory drug, or a shift in an environmental condition such as temperature. Most conveniently, the difference between the two conditions is temperature, and such a conditionally-sensitive virus is thus referred to as a temperature-sensitive helper virus.

Helper virus may be prepared in any cell that is permissive for viral replication. For adenovirus, preferred cells include 293 cells and HeLa cells. It is preferable to employ culture techniques that permit an increase in seeding density. 293 cells and HeLa cell variants are available that have been adapted to suspension culture. HeLa is preferable for reasons of cell growth, viability and morphology in suspension. These cells can be grown at sufficient density ($2 \times 10^6$ per ml) to make up for the lower replication rate of the temperature-sensitive adenovirus strain. Once established, cells are infected with the virus and cultured at the permissive temperature for a sufficient period; generally 3–7 days and typically about 5 days.

Examples of methods useful for helper virus preparation, isolation and concentration can be found in Atkinson et al. (WO 99/11764).

Several criteria influence selection of cells for use in producing rAAV particles as described herein. As an initial matter, the cell must be permissive for replication and packaging of the rAAV vector when using the selected helper virus. However, since most mammalian cells can be productively infected by AAV, and many can also be infected by helper viruses such as adenovirus, it is clear that a large variety of mammalian cells and cell lines effectively satisfy these criteria. Among these, the more preferred cells and cell lines are those that can be easily grown in culture so as to facilitate large-scale production of rAAV virus preparations. Again, however, many such cells effectively satisfy this criterion. Where large-scale production is desired, the choice of production method will also influence the selection of the host cell. For example, as described in more detail in Atkinson et al. (WO 99/11764) and in the art, some production techniques and culture vessels or chambers are designed for growth of adherent or attached cells, whereas others are designed for growth of cells in suspension. In the latter case, the host cell would thus preferably be adapted or adaptable to growth in suspension. However, even in the case of cells and cell lines that are regarded as adherent or anchorage-dependent, it is possible to derive suspension-adapted variants of an anchorage-dependent parental line by serially selecting for cells capable of growth in suspension: See, for example, Atkinson et al. (WO 99/11764).

Ultimately, the helper virus, the rAAV vector sequence, and all AAV sequences needed for replication and packaging must be present in the same cell. Where one or more AAV packaging genes are provided separately from the vector, a host cell is provided that comprises: (i) one or more AAV packaging genes, wherein each said AAV packaging gene encodes an AAV replication or encapsidation protein; (ii) a heterologous polynucleotide introduced into said host cell using an rAAV vector, wherein said rAAV vector comprises said heterologous polynucleotide flanked by at least one AAV ITR and is deficient in said AAV packaging gene(s); and (iii) a helper virus or sequences encoding the requisite helper virus functions. It should be noted, however, that one or more of these elements may be combined on a single replicon.

The helper virus is preferably introduced into the cell culture at a level sufficient to infect most of the cells in culture, but can otherwise be kept to a minimum in order to limit the amount of helper virus present in the resulting preparation. A multiplicity of infection or "MOI" of 1–100 may be used, but an MOI of 5–10 is typically adequate.

Similarly, if the rAAV vector and/or packaging genes are transiently introduced into the packaging cell (as opposed to being stably introduced), they are preferably introduced at a level sufficient to genetically alter most of the cells in culture. Amounts generally required are of the order of 10 µg per $10^6$ cells, if supplied as a bacterial plasmid; or $10^8$ particles per $10^5$ cells, if supplied as an AAV particle. Determination of an optimal amount is an exercise of routine titration that is within the ordinary skill of the artisan.

These elements can be introduced into the cell, either simultaneously, or sequentially in any order. Where the cell is inheritably altered by any of the elements, the cell can be selected and allowed to proliferate before introducing the next element.

In one preferred example, the helper virus is introduced last into the cell to rescue and package a resident rAAV vector. The cell will generally already be supplemented to the extent necessary with AAV packaging genes. Preferably, either the rAAV vector or the packaging genes, and more preferably both are stably integrated into the cell. It is readily appreciated that other combinations are possible. Such combinations are included within the scope of the invention.

Once the host cell is provided with the requisite elements, the cell is cultured under conditions that are permissive for the replication AAV, to allow replication and packaging of the rAAV vector. Culture time is preferably adjusted to correspond to peak production levels, and is typically 3–6 days. rAAV particles are then collected, and isolated from the cells used to prepare them.

Optionally, rAAV virus preparations can be further processed to enrich for rAAV particles, deplete helper virus particles, or otherwise render them suitable for administration to a subject. See Atkinson et al. for exemplary techniques (WO 99/11764). Purification techniques can include isopynic gradient centrifugation, and chromatographic techniques. Reduction of infectious helper virus activity can include inactivation by heat treatment or by pH treatment as is known in the art. Other processes can include concentration, filtration, diafiltration, or mixing with a suitable buffer or pharmaceutical excipient. Preparations can be divided into unit dose and multi dose aliquots for distribution, which will retain the essential characteristics of the batch, such as the homogeneity of antigenic and genetic content, and the relative proportion of contaminating helper virus.

Various methods for the determination of the infectious titer of a viral preparation are known in the art. For example, one method for titer determination is a high-throughput titering assay as provided by Atkinson et al. (WO 99/11764). Virus titers determined by this rapid and quantitative method closely correspond to the titers determined by more classical techniques. In addition, however, this high-throughput method allows for the concurrent processing and analysis of many viral replication reactions and thus has many others uses, including for example the screening of cell lines permissive or non-permissive for viral replication and infectivity.

Uses for Recombinant Viral Vectors of the Invention

The recombinant viral vectors of the invention, especially the parvovirus vectors such as rAAV vectors, are useful in several contexts, including gene therapy and genomics screening. For example, because rAAV vectors based on a native AAV genome require host cell functions and helper functions for formation of a RF, expression of inserted heterologous sequences from such vectors is often inefficient. A significant period of time, often on the order of weeks, can be required to obtain useful levels of a gene product of interest. In contrast, the metabolically activated vectors of the invention can efficiently and rapidly form duplex templates for transcription, thereby providing enhanced expression of transgenes and reducing the time required for accumulation of a gene product of interest to days, rather than weeks. Since the metabolically activated vectors of the invention provide more rapid and efficient expression of a transgene, they will also facilitate procedures known in the art in which rapid expression of a gene product of interest is desirable. These procedures include, for example, genomics screening, target identification and target validation.

In some embodiments, a recombinant viral vector of the invention is used to introduce a sequence of interest into a host cell, such as a bacterial or eukaryotic cell, such as a mammalian cell. Preferably, the recombinant viral vector is a parvovirus vector, such as an rAAV vector. Introduction into a host cell is accomplished by contacting the cell with a recombinant viral vector of the invention under conditions which allow uptake of exogenous nucleic acid such that the recombinant viral vector(s) is introduced into the cell. In some embodiments, the invention provides methods of introducing a polynucleotide of interest into a host cell, via a recombinant virus particle containing a recombinant virus vector of the invention, such as a recombinant AAV containing an rAAV vector of the invention, comprising contacting the cell with the recombinant virus particle under conditions which allow infection, whereby the recombinant viral vector is introduced into the cell. An exogenous polynucleotide sequence is thereby introduced into the cell.

In other embodiments, the recombinant viral vectors of the invention are used for the expression of a polynucleotide, such as gene products of interest, in a host cell such as a mammalian cell. These methods comprise subjecting the cell containing a recombinant viral vector, preferably a parvovirus vector such as an rAAV, to conditions which allow expression, whereby a coding region of the heterologous sequence of the recombinant viral vector is expressed. Gene products include, but are not limited to RNAs, such as, for example, antisense RNAs and ribozymes, and proteins, such as, for example, enzymes, structural proteins, and cytokines. As described above, a heterologous sequence encoding the gene product may be operably linked to one or more sequences regulating its expression such as, for example, promoters and enhancers.

In some embodiments, introduction of and/or expression from a recombinant vector of the invention is accomplished by transduction, in which a recombinant viral particle containing a recombinant viral vector of the invention (such as an rAAV particle containing an rAAV as described herein) is contacted with a host cell under conditions which are favorable to viral infection and/or expression of the heterologous sequence, such that the recombinant viral vector is introduced and/or expressed in the host cell.

Types of cells into which the polynucleotides of the invention can be introduced include, but are not limited to, eucaryotic cells, procaryotic cells and Archaea. Eucaryotic cells include animal cells, plant cells, yeast cells and, in a preferred embodiment, mammalian cells, more preferably, human cells, mammalian, including human, cells include cell lines as well as primary cells, such as primary foreskin fibroblasts.

Introduction of nucleic acids into cells can be achieved by methods known in the art including, but not limited to, microinjection, transfection, electroporation, calcium phosphate co-precipitation, DEAE-dextran, lipid-mediated gene transfer, and particle bombardment. Within a population of cells that have been contacted with an rAAV the vector polynucleotide, expression of reporter function identifies a cell in which a vector polynucleotide has been introduced into the cell.

A population of cells wherein many, and preferably most, cells carry an integrated vector (i.e., a library of marked cells) can be obtained by employing negative selection against cells that do not express the reporter gene. One illustrative, non-limiting method for negative selection involves growing cells that have been contacted with the vector in the presence of a cytotoxic drug for which the reporter gene provides resistance. In this case, cells not expressing the reporter gene do not grow in the presence of the drug.

Following introduction of vector polynucleotides into cells, selection for cells in which a vector polynucleotide has been introduced can be performed according to standard methods. As an illustration, if a reporter gene is used, such as a neomycin resistance gene, cells are grown in medium containing G418, which is a cytotoxic drug that prevents growth of cells that do not express neomycin resistance. After an appropriate period of contact with the medium, clones of neomycin-resistant cells are obtained, that are suitable for expansion into larger populations of cells using standard cell culture techniques. Alternatively, if lacZ is used as a reporter gene, marked cells can be selected by, for example, colony color (using a chromogenic β-galactosidase substrate) or by fluorescence-activated cell sorting (FACS), selecting for cells that express β-galactosidase activity.

In certain embodiments, a viral vector of the invention, such as an rAAV vector, after introduction into a host cell, can stably integrate into the genome of the cell. In these circumstances, long-term persistence and expression of the transgene is obtained, without disturbing normal cellular metabolism. Thus, a continuous source of transgene product is provided, and ongoing administration of the gene product is achieved, in the host cell. This is a distinct and significant advantage compared to other treatment modalities, most of which confer only transient benefits.

Administration of a recombinant viral vector of the invention to a mammalian subject, so as to introduce a sequence of interest into a mammalian cell and/or express a gene product of interest in a mammalian cell can be accomplished in several ways, and is described herein using parvovirus vectors, especially rAAV, as an example. Preferred modes of administration include, but are not limited to, intramuscular delivery, intravenous delivery, and direct injection of the composition(s) to a tissue or anatomical site. Injection can be, for example, intra-arterial, intravenous, intramuscular or intra-articular. Methods of transducing cells of blood vessels are described, for example, in PCT US97/103134.

Another preferred mode of administration of compositions of the invention is through naso-pharyngeal and pulmonary routes. These include, but are not limited to, inhalation, transbronchial and transalveolar routes. The invention includes compositions suitable for administration by inhalation including, but not limited to, various types of aerosols and powder forms. Devices suitable for administration of compositions by inhalation include, but are not limited to, atomizers and vaporizers.

An effective amount of recombinant viral vector, such as rAAV (preferably in the form of AAV particles) is administered, depending on the objectives of treatment. An effective amount may be given in single or multiple doses. Where a low percentage of transduction can achieve a therapeutic effect, the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, preferably at least about 80%, more preferably at least about 95%, and even more preferably at least about 99% of the cells of the desired tissue type.

As an guide, the number of parvovirus particles, such as rAAV particles, administered per injection will generally be between $1 \times 10^6$ and $1 \times 10^{14}$ particles, preferably, between $1 \times 10^7$ and $1 \times 10^{13}$ particles, more preferably $1 \times 10^9$ and $1 \times 10^{12}$ particles and even more preferably about $1 \times 10^{11}$ particles.

The number of parvovirus particles, such as rAAV particles, administered per intramuscular injection and per intravenous administration, for example, will generally be at least about $1 \times 10^{10}$, and is more typically $5 \times 10^{10}$, $1 \times 10^{11}$, $5 \times 10^{11}$, $1 \times 10^{12}$, $5 \times 10^{12}$ and on some occasions $1 \times 10^{13}$ particles, including both DNAse resistant and DNAse susceptible particles. In terms of DNAse resistant particles, the dose will generally be between $1 \times 10^6$ and $1 \times 10^{14}$ particles, more generally between about $1 \times 10^{10}$ and $1 \times 10^{13}$ particles.

The effectiveness of viral delivery can be monitored by several criteria. For example, samples removed by biopsy or surgical excision can be analyzed by in situ hybridization, PCR amplification using vector-specific probes, and/or RNAse protection to detect viral DNA and/or viral mRNA, such as rAAV DNA or RNA. Also, for example, harvested tissue, joint fluid and/or serum samples can be monitored for the presence of a protein product encoded by the recombinant viral vector with immunoassays, including, but not limited to, immunoblotting, immunoprecipitation, immunohistology and/or immunofluorescent cell counting, or with function-based bioassays. Examples of such assays are known in the art.

The invention also provides methods in which ex vivo strategies are used for administration of recombinant viral vectors described herein to deliver a transgene to an individual, preferably a mammal. Such methods and techniques are known in the art. See, for example, U.S. Pat. No. 5,399,346. Generally, cells are removed from an individual, transduced by recombinant viral vectors, such as rAAV vectors, in vitro, and the transduced cells are then reintroduced into the indiivdual. Cell suitable for ex vivo delivery are known to those skilled in the art and include, for example, various types of stem cells.

The selection of a particular composition, dosage regimen (i.e., dose, timing and repetition) and route of administration will depend on a number of different factors, including, but not limited to, the subject's medical history and features of the condition and the subject being treated. The particular dosage regimen may be determined empirically.

In one embodiment of the invention, methods for identifying a phenotype associated with expression of a coding sequence of a recombinant viral vector of the invention, preferably a parvovirus vector such as an rAAV vector of the invention, are provided, comprising subjecting host cells containing a recombinant viral vector of the invention to conditions which allow expression; comparing a phenotype of these expressing cells to a phenotype of cells which lack the recombinant viral vector; wherein a phenotypic difference indicates a phenotype associated with expression of the coding sequence. In other embodiments, phenotypic screening is accomplished by contacting a host cell with a recombinant viral vector described herein under conditions that allow uptake of the vector; assaying the cell for expression of the heterologous coding region of the vector; comparing a phenoetype of the cell expressing the heterologous coding region with a phenotype of a cell that lacks the vector. A phenotypic difference indicates that the phenotype of the cell expression the heterologous sequence is a phenotype associated with expression of the coding region. Such phenotypic characteristics could in turn provide valuable information regarding function(s) of the coding sequence, as well as its potential role in health or contributing to disease states, and as a useful drug target.

EXAMPLES

The following examples are provided to illustrate, but not limit, the invention.

Example 1

Construction of a Half-size AAV Vector

Figure 5D:
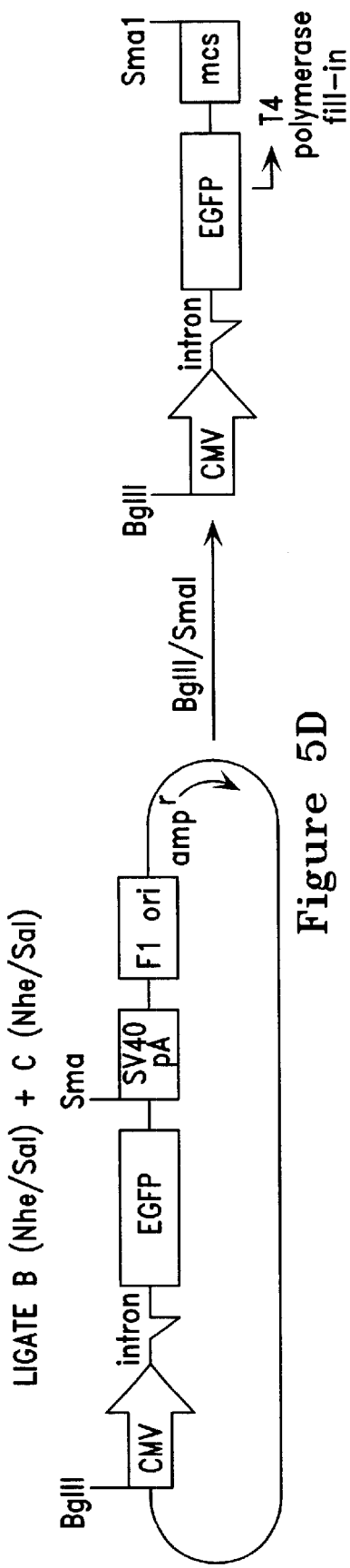
Figure 5E:
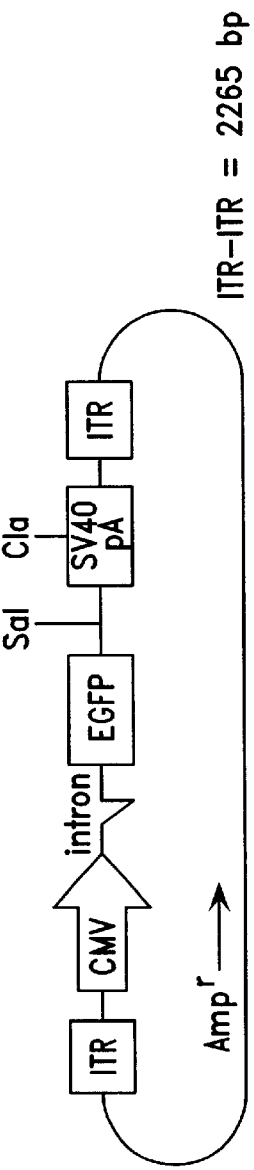

An AAV vector (AAV-cmv-intron-EGFP, also known as rAAV-GFP(0.5)), designed to express the GFP gene and to have a size not more that 50% of the size of an AAV genome, was constructed as shown in FIG. 5. A NheI to SalI fragment from pEGFP-C1 (Clontech), containing EGFP (FIG. 5C), was ligated to the large NheI to SalI fragment obtained from plasmid pCI (Promega, FIG. 5B). The resulting plasmid construct was then digested with BglII and SmaI, filled in using nucleoside triphosphates and T4 DNA polymerase (FIG. 5D), and ligated to a XhoI to SpeI fragment from AAV-syn pA (FIG. 5A), which had been filled in using T4 DNA polymerase. The final construct (FIG. 5E) is 2265 base pairs from the start of the 5' ITR to the end of the 3' ITR.

Example 2

Construction of Full-size AAV Vectors

Two full-size AAV vectors, designed to express the GFP gene and to have a size approximately equivalent to the size of an AAV genome, were constructed as shown in FIG. 6.

Figure 6A:
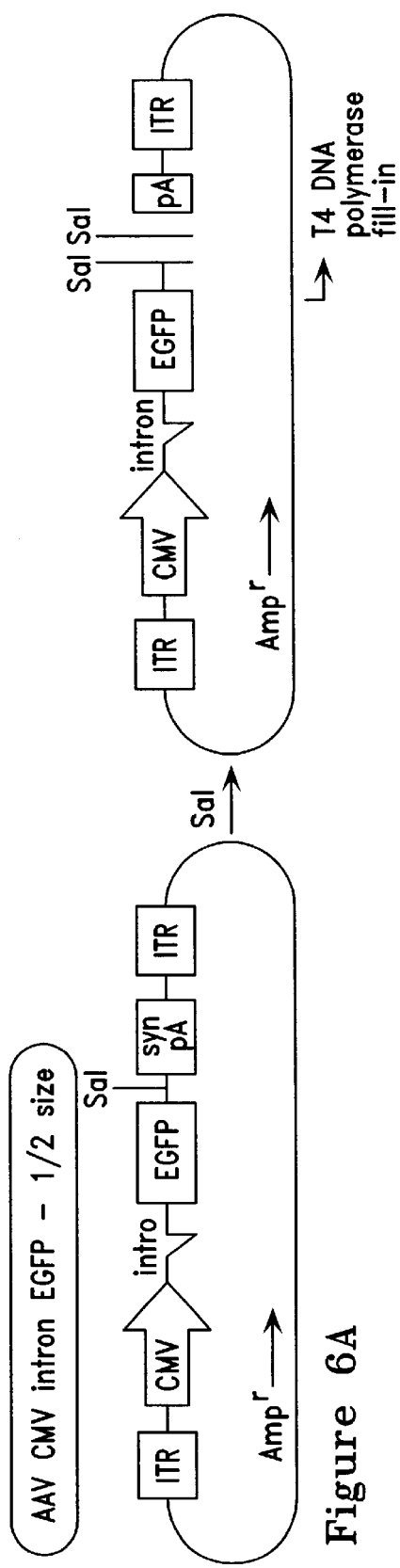
FIGS. 6A–6F illustrate two strategies for the construction of full-size AAV-GFP vectors.
Figure 6B:
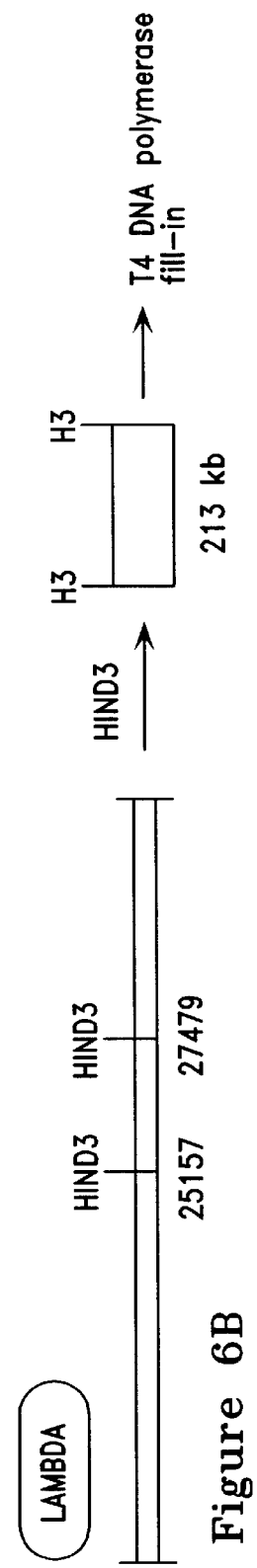
Figure 6C:
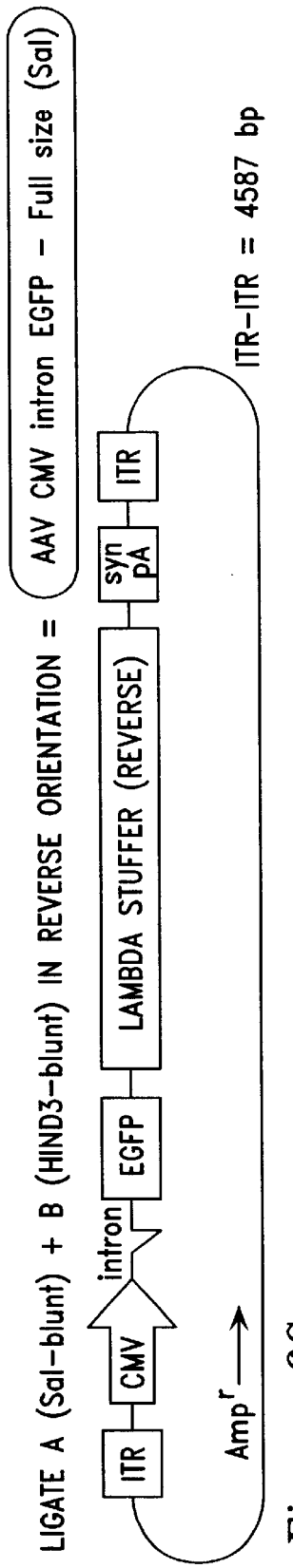

The first full size vector (Sal-AAV-cmv-intron-EGFP, also known as rAAV-GFP(Sal)), was constructed by ligating a 2.3 kb HindIII fragment of lambda phage DNA (filled in using nucleoside triphosphates and T4 DNA polymerase, FIG. 6B) to the half-size vector described in example 1, that had been digested with SalI and filled-in with T4 DNA polymerase (FIG. 6A). The final full-size Sal-AAV-cmv-intron-EGFP construct (FIG. 6C) is 4587 nucleotides long from the start of the 5' ITR to the end of the 3' ITR.

Figure 6D:
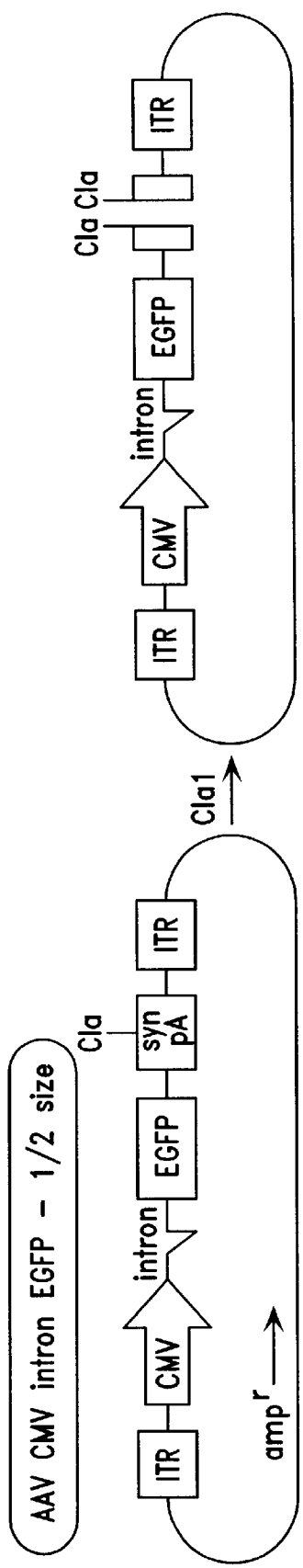
Figure 6E:
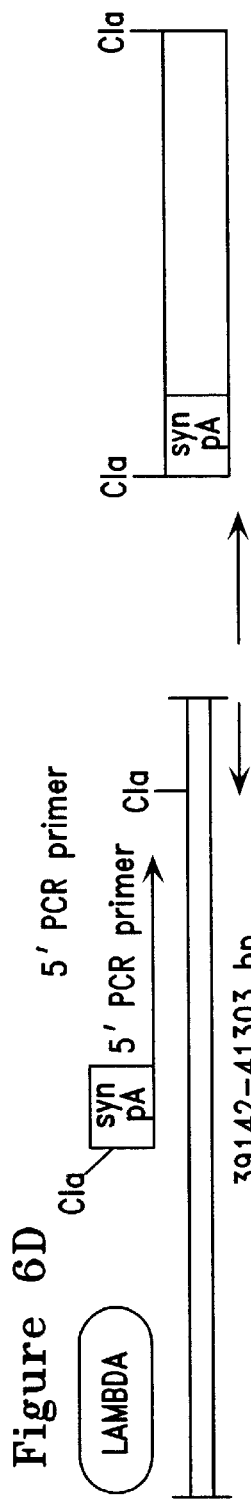
Figure 6F:
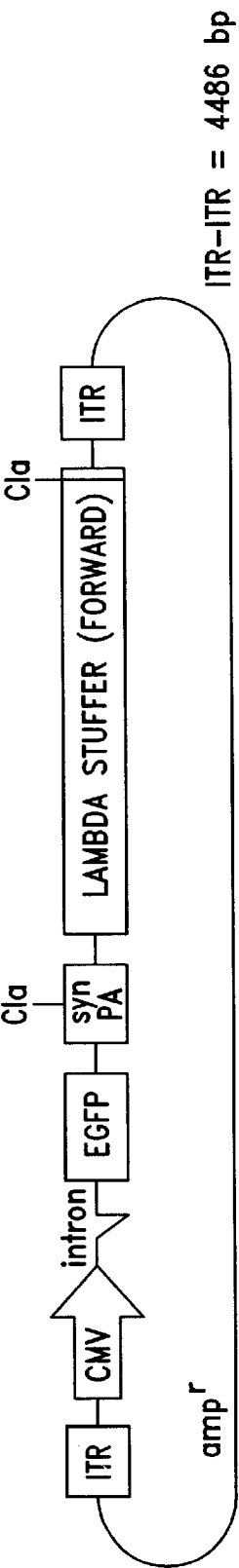

The other full-size vector (Cla-AAV-cmv-intron-EGFP, also known as rAAV-GFP(Cla)) was constructed by ligating a 2.3 kb ClaI fragment (obtained from lambda phage DNA by PCR, FIG. 6E)) to the vector described in Example 1 that had been digested with ClaI (FIG. 6D). The final full size Cla-AAV-cmv-intron-EGFP construct (FIG. 6F) is 4486 nucleotides long from the start of the 5' ITR to the end of the 3' ITR.

Each of these full-size vectors thus contains the same sequences as the half size vector, with the addition of a stuffer fragment from lambda DNA inserted either in front of (full-size Sal) or behind (full-size Cla) the synthetic polyA addition site.

Example 3

Analysis of Expression From Half-size and Full Size Vector Plasmids

The half-size and full-size plasmids, described in the previous examples, were used to transfect human 293 and HeLa cells to assess the level of expression of the GFP protein obtained from each construct. Expression levels from the AAV constructs were compared to the level obtained after transfection of the plasmid EGFP-C1 (FIG. 5C). Equimolar amounts of each plasmid were introduced into each cell line, and, at 48 hr after transfection, the amount of GFP expression was assessed by analysis in a flow cytometer. Results are shown in Table 1.

TABLE 1

Analysis of expression from vector plasmids

| Cell type | construct | DNA amount (equimolar) | fluorescent cells (%) | % of Parental |
|---|---|---|---|---|
| 293A | EGFP-C1 (parental) | 1.0 µg | 94 | 100 |
| 293A | AAV-GFP ½ size | 1.0 µg | 92 | 98 |
| 293A | AAV-GFP full size-Cla | 1.0 µg | 81 | 86 |
| 293A | AAV-GFP full size-Sal | 1.0 µg | 89 | 95 |
| 293A | EGFP-C1 (Parental) | 0.3 µg | 86 | 100 |
| 293A | AAV-GFP ½ size | 0.3 µg | 83 | 97 |
| 293A | AAV-GFP full size-Cla | 0.3 µg | 59 | 69 |
| 293A | AAV-GFP full size-Sal | 0.3 µg | 82 | 95 |
| HeLa | EGFP-C1 (Parental) | 1.0 µg | 81 | 100 |
| HeLa | AAV-GFP ½ size | 1.0 µg | 80 | 99 |
| HeLa | AAV-GFP full size-Cla | 1.0 µg | 68 | 84 |
| HeLa | AAV-GFP full size-Sal | 1.0 µg | 67 | 83 |
| HeLa | EGFP-C1 (Parental) | 0.3 µg | 77 | 100 |
| HeLa | AAV-GFP ½ size | 0.3 µg | 74 | 96 |
| HeLa | AAV-GFP full size-Cla | 0.3 µg | 55 | 71 |
| HeLa | AAV-GFP full size-Sal | 0.3 µg | 65 | 84 |

These results indicate that, in general, the half-size vector and the full-size Sal vector were expressed in equivalent numbers of cells, on a molar basis with respect to the gene, to that obtained from the reference plasmid EGFP-C1. Expression of GFP from the full-size Cla plasmid was generally lower. Therefore, in subsequent examples, comparisons were conducted between the full-size Sal vector and the half-size vector.

Example 4 rAAV Particles Derived From Half-size or Full-size Vector Plasmids

Preparations of AAV vector particles derived from either half-size or full-size vector Plasmids were produced using the producer cell line C12. C12 is a HeLa cell line containing a rep and cap gene cassette, in which Rep and Cap expression is induced upon infection with adenovirus. When C12 cells are concurrently infected with adenovirus and transfected with a vector plasmid, the vector genome is amplified and packaged into AAV particles.

Forty T225 flasks, seeded with C12 cells, were infected with adenovirus type 5 (at a multiplicity of 10 infectious units per cell) one hour prior to transfection. Cells were transfected with plasmid DNA by the DEAE-dextran method and were incubated for four hours at 37° C., in a 10% $CO_2$ atmosphere. Medium was aspirated and cells were shocked by adding medium containing 10% DMSO for 5 minutes at room temperature. The DMSO-containing medium was then replaced with complete medium and cells were incubated for 72 hours at 37° C., 10% $CO_2$. Cells were then scraped into medium and pelleted by centrifugation at 3,000 rpm for 10 minutes. Then medium was aspirated and the cell pellet was resuspended in 10 mM Tris, 10 mM $MgCl_2$, pH 8.1. The cells were lysed by one rapid freeze/thaw cycle followed by sonication (4 pulses of 15 seconds each). BENZONASE® was added to the lysate to a concentration of 2,500 units/ml and the lysate was incubated at 37° C. for 1 hour. CsCl was added to the benzonaseg®-treated lysate to a final refractive index of 1.3710. The lysates were transferred to a centrifuge tube, overlaid with 0.5 ml mineral oil and centrifuged in a swinging bucket rotor (SW41) at 35,000 rpm, 15° C. for 48 hours. The region of the CsCl gradient starting at 1 cm from the bottom of the tube up to, but not including, the adenovirus band was pooled and dialyzed against 50 mM Tris, 5 mM $MgCl_2$, 1 mM EDTA, 5%(v/v) glycerol, 100 mM NaCl, pH 7.4 (TMEG+NaCl) for 3 hours with one buffer exchange. The dialyzed pool was purified by column chromatography and fractions were assayed to locate the peak fractions of recombinant adeno-associated virus particles (rAAV). Peak fractions were pooled and dialyzed for 3 hours with one buffer exchange against Ringer's buffered salt solution (RBSS) containing 5%(v/v) glycerol. The dialyzed pool of vector was filtered through a 0.22 µm filter, divided into aliquots and stored at −70° C.

Example 5

Analysis of rAAV Titer and Determination of rAAV Infectivity

The number of vector particles in vector preparations was estimated by measuring the number of DNAse resistant particles (DRP) using a slot blot DNA hybridization assay. Vector samples (40 µl) were treated with DNAse, by mixing with 32 µl of 2×DNAse buffer (containing 80 mM Tris pH 7.5, 12 mM $MgCl_2$, 4 mM $CaCl_2$) and 8 µl of DNAse (10 U/ml) and incubating at 37° C. for 20 minutes. The reaction was stopped by adding 4 µl of 0.5 M EDTA and 116 µl of water, and incubating at room temperature for 5 minutes. The reaction mixture was then added to 1 ml of denaturation solution (containing 0.4 N NaOH, 1 µg/ml salmon sperm DNA, 10 mM EDTA, pH 8.0) at room temperature. Portions (1 µl and 10 µl) of the denatured material were transferred to a hybridization filter in a slot blot apparatus. Plasmid standards were co-transferred to separate regions of the filter. The blot was hybridized with a random primed $^{32}$P-labeled GFP DNA probe. The number of DRP was calculated by comparison with the standards and the amount of vector particles in each preparation was expressed as DRP/ml.

The infectivity of vector preparations was determined using a replication assay in clone 37 (C37) cells. Atkinson et al. (1998) *Nucleic Acids Res.* 26:2821–2823. C37 cells are a HeLa cell line containing the AAV rep and cap genes. When C37 cells are infected with adenovirus, expression of the rep gene permits replication of a coinfecting AAV vector. See PCT publication WO 96/17947.

To determine vector infectivity, C37 cells seeded in 96-well plates were coinfected with adenovirus 5 (at a multiplicity of 10 infectious units per cell) together with 3-fold serial dilutions of either a rAAV-GFP vector or the tgACAPSN vector, as a standard. The tgACAPSN vector is a rAAV vector that contains, in the following order: an AAVITR, a CMV promoter sequence, a human alkaline phosphatase cDNA, a SV40 promoter, a bacterial neomycin resistance gene, a polyadenylation sequence and an AAV ITR. See, for example, PCT WO 97/32990; PCT WO 99/20779; and Lynch et al. (1997) *Circ. Res.* 80:497–505. At 72 hours post-infection, denaturation solution (0.4 M NaOH, 1 mM EDTA) was added to each well and the plates were incubated at 65° C. for 60 minutes. Denatured samples were vacuum-blotted onto a membrane, followed by washing with 0.4M NaOH, and nucleic acids were crosslinked to the membrane by UV irradiation. The blot was hybridized with a random primed $^{32}$P labeled CMV DNA probe. The infectivity of the vector preparation, expressed as replication units (Atkinson et al., supra), was determined by comparison with the tgACAPSN standard.

Determinations of particle number (DRP) and infectivity were used to calculate the particle:infectivity ratio for the vector preparations. For rAAV derived from the half-size vector plasmid rAAV-GFP(0.5) this ratio was 58 and for rAAV derived from the full size vector rAAV-GFP(Sal) this ratio was 52. Thus both vectors generated particles of equivalent infectivity. The rAAV containing an rAAV vector derived from the half-size vector plasmid will be denoted in these Examples as the "half-complexity" rAAV vector (or "0.5").

Example 6

Expression in Human 293 Cells by rAAV Containing rAAV Vectors

Human 293 cells were infected with either the half-complexity rAAV (rAAV derived from the half-size rAAV-GFP(0.5) vector plasmid) or the rAAV derived from the rAAV-GFP(Sal) vector, and the number of cells expressing GFP protein was determined by fluorescence microscopy.

293A (7×10$^3$ cells/well) were seeded into 48-well plates. The next day the cells, in 0.2 ml of medium, were infected at a multiplicity of either 100 or 1000 DRP per cell. At 24 hours after infection, the medium was replaced with 0.5 ml fresh medium. At 48 hours and 72 hours after infection, the number of cells expressing GFP protein was counted using a fluorescence microscope. The results, presented in Table 2, show that the half-complexity vector had a significantly higher ability to express detectable levels of GFP as indicated by percentage of fluorescent 293 cells, compared to the full-size vector.

TABLE 2

Expression in human 293 cells by rAAV vectors

| vector | dose DRP/cell | time after infection (hr) | Fluorescent cells (%) (n = 2) | fold difference |
|---|---|---|---|---|
| rAAVGFP(0.5) | 100 | 48 | 10.2% | >10 |
| rAAVGFP(Sal) | 100 | 48 | 0.0% | |
| rAAVGFP(0.5) | 1000 | 48 | 63.6% | 3.6 |
| rAAVGFP(Sal) | 1000 | 48 | 17.7% | |
| rAAVGFP(0.5) | 100 | 72 | 13.1% | 10.9 |
| rAAVGFP(Sal) | 100 | 72 | 1.2% | |
| rAAVGFP(0.5) | 1000 | 72 | 72.2% | 5.6 |
| rAAVGFP(Sal) | 1000 | 72 | 12.9% | |

Example 7

Expression in HeLa Cells by rAAV Vectors

HeLa cells were infected with either the half-complexity (derived from rAAV-GFP(0.5)) vector or the rAAV-GFP (Sal) vector, and the number of cell expressing GFP protein was determined by fluorescence microscopy and by flow cytometry.

HeLa 5 cells ($2.5 \times 10^4$ cells/well) were seeded into 24-well plates. The next day the cells, in 0.5 ml of medium, were infected at a multiplicity of either 100 or 1000 DRP per cell. At 24 hours after infection, the medium was replaced with 1.0 ml fresh medium. At 72 hours after infection, the number of cells expressing GFP protein was determined both by fluorescence microscopy and also by analysis in a flow cytometer. The results, presented in Table 3, show that the half-complexity vector had a significantly higher ability to express detectable levels of GFP as indicated by percent of fluorescent HeLa cells, compared to the full-size vector, as measured by both methods. Both methods provided similar estimates of GFP expression. HeLa cells are generally considered to express transgenes from rAAV only inefficiently. At the higher MOI, there was a significantly higher-fold increase in expression in the HeLa cells when compared to the 293 cells.

TABLE 3

Expression HeLa cells by rAAV vectors

| vector | dose (DRP/ml) | fluorescent cells (%) by microscopy (n = 2) | fold difference | fluorescent cells (%) by flow (n = 3) | fold difference |
|---|---|---|---|---|---|
| rAAV-GFP (0.5) | 100 | 9.0 | 9 | 9.8 | 9.8 |
| rAAV-GFP (Sal) | 100 | 1.0 | | 1.0 | |
| rAAV-GFP (0.5) | 1000 | 49.4 | 15 | 47.9 | 16 |
| rAAV-GFP (Sal) | 1000 | 3.3 | | 3.0 | |

Example 8

Analysis of vector DNA genomes in rAAV particles

To analyze the DNA genomes from vector particles, DNA was extracted from the vector particles and analyzed by gel electrophoresis under denaturing (alkaline gel) or non-denaturing (neutral gel) conditions. In preparation for electrophoretic analysis, rAAV vector samples were treated with SDS and proteinase K, incubated at 50° C. for 4 hours, extracted successively with phenol, phenol/chloroform, and chloroform. Nucleic acid was then precipitated with ethanol, resuspended and loaded onto either an alkaline or neutral agarose gel.

Alkaline gel electrophoresis was conducted on a gel of 1.5% SeaKem® (FMC Products) agarose gel in 30 mM NaOH and 2 mM EDTA, with a running buffer of 30 mM NaOH, 2 mM EDTA. Loading buffer for the alkaline gel was 30 mM NaOH, 2 mM EDTA, 10% glycerol and 0.1% bromcreosol green (final concentrations). The alkaline gel was run overnight at 20 volts with recirculation of the running buffer.

The neutral gel was 1.0% SeaKem® (FMC Products) agarose in 0.45 M Tris-borate, 0.001 M EDTA (TBE). The neutral gel was run overnight at 40 volts.

Analysis of the gels was conducted as follows. Gels were subjected to denaturing conditions, then neutralized and blotted overnight onto a nylon membrane. The blot was crosslinked and hybridized with a random primed $^{32}$P labeled GFP probe using "quick hyb®" solution (Stratagene, La Jolla, Calif., Catalogue #201220). Hybridized blots were exposed to x-ray film and the results are shown in FIG. 7.

Figure 7A:
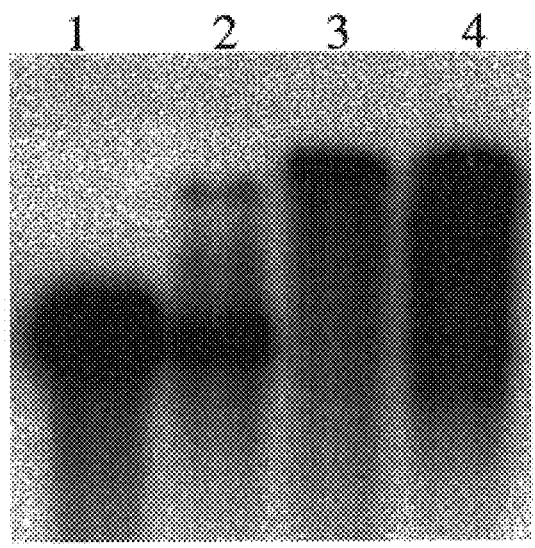
FIGS. 7A–B are half-tone reproductions of agarose gel electrophoresis analysis of vector DNA from virus particles. Molecular weight values, determined by parallel analysis of markers, are shown to the left.
Figure 7B:
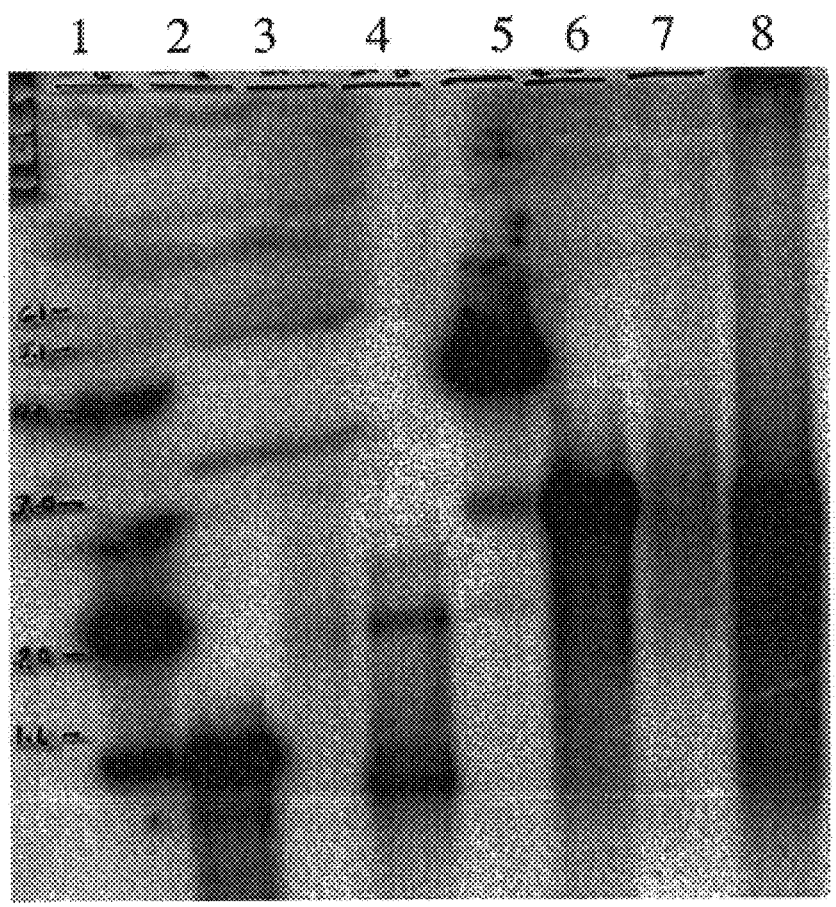

Alkaline gel analysis, shown in FIG. 7A, indicates that preparations of virus particles having vector genomes that were made from a half-size plasmid contain DNA molecules that have a single-stranded length that is the same as a native AAV genome (second lane from left). This is what would be expected if "snap-back"-type RF molecules have been packaged in these virus particles. Similarly, when viral genomes are subjected to denaturing conditions, then analyzed at neutral pH (as shown in FIG. 7B), a significant portion of the genomes from viruses made from half-size vectors do not denature, migrating at a position (FIG. 7B, Track 4) similar to that of non-denatured half-size duplex fragment (FIG. 7B, Track 1).

Thus, rAAV vectors that are present in rAAV virus particles made from half-size plasmids (i.e., half-complexity) have a length that is the same size as a native AAV genome and possess significant secondary structure presumably in the form of intrastrand base pairing. In fact, the analysis presented in this example indicates that the entire genome of such vectors is base-paired.

Example 9

Analysis of Vector Genomes in Infected Cells

Vector genomes were extracted from HeLa cells after infection with rAAV virus particles containing half-complexity vectors (i.e., vectors derived from either a half-size (which results in a self complementary single stranded polynucleotide having approximately 50% sequence complexity)) or containing control full-size vector genome and with or without coinfection with adenovirus. The extracted vector genomes were analyzed by electrophoresis in alkaline and neutral agarose gels, as described in Example 8.

HeLa cells ($2.5 \times 10^5$ cells/well) were seeded into 6-well plates. The next day, the cells were infected, in 1 ml complete medium, with rAAV containing rAAV vectors derived from either a full-size or a half-size vector genome (which results in a full-sized molecule of approximately 50%, or half, sequence complexity), as described in Example 8. At 6, 24, 48 and 72 hours after infection with rAAV alone (at a multiplicity of 500 DNase resistant particles per cell), or at 6 hours after infection with rAAV together with adenovirus (at a multiplicity of 5 infectious units per cell), cells were harvested and vector DNA was selectively extracted using the Hirt SDS-high salt precipitation procedure. Briefly, cells were scraped into medium, centrifuged at 1,500 rpm for 10 min, resuspend in 0.5 ml lysis buffer (0.6% SDS, 10 mM EDTA), adjusted to 1 M NaCl by addition of 0.15 ml of 5 M NaCl and incubated at 4° C. overnight. The lysate was then centrifuged at 14,000 rpm for 10 min and the supernatant was transferred to a fresh tube. After addition of 20 μl of 10% SDS and 2.5 μl of a 10 mg/ml solution of proteinase K, the lysate was incubated at 50° C. for 4 hours then extracted with phenol, phenol/chloroform and chloroform. DNA was precipitated from the aqueous phase with ethanol, and the precipitated DNA was resuspended in 50 μl water. Aliquots (25 μl) of the resuspended DNA were loaded onto alkaline and neutral agarose gels. Electrophoresis and analysis of gels was conducted as described in Example 8.

Figure 8A:
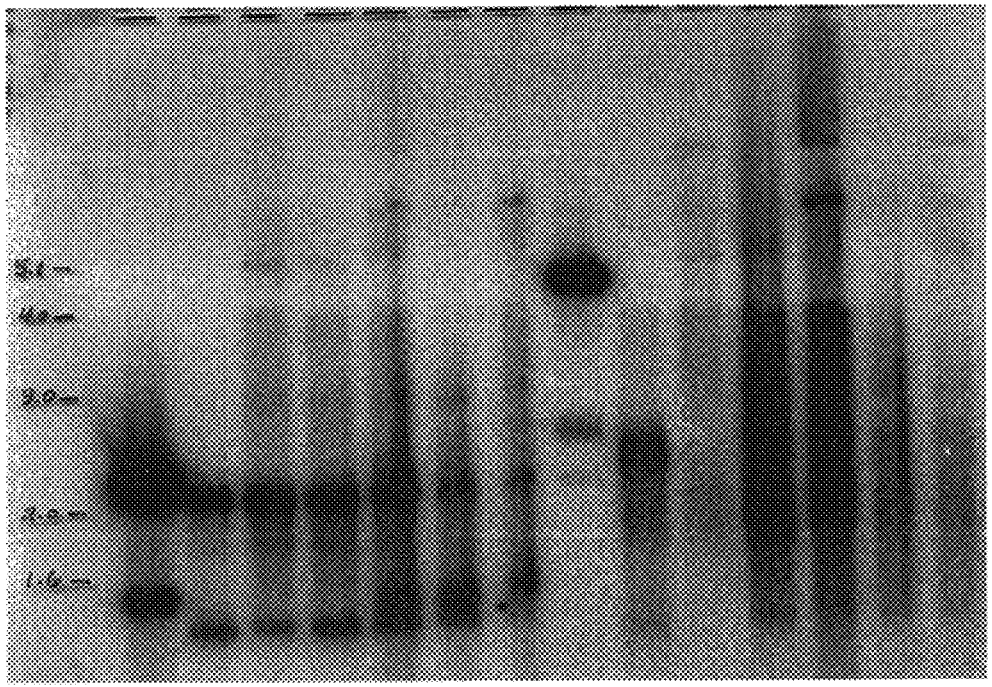
FIGS. 8A–B are half-tone reproductions of agarose gel electrophoresis analysis of vector DNA genomes from infected cells.
Figure 8B:
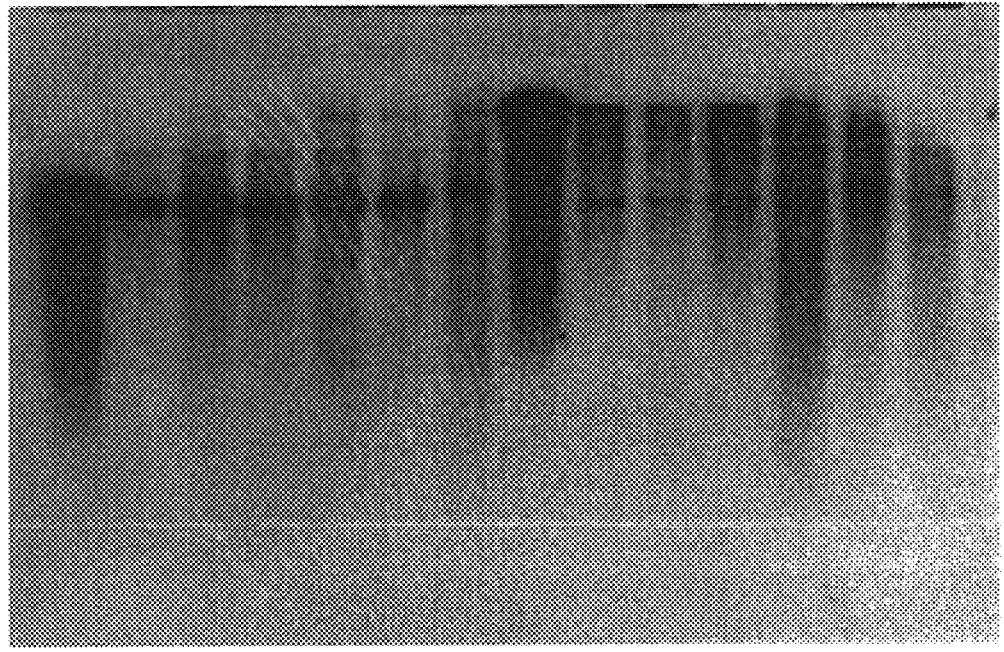

The results are shown in FIG. 8 (FIG. 8A shows a neutral gel and FIG. 8B shows an alkaline gel) and indicate that, in infected cells, the rAAV of half-complexity (i.e., derived from a half-size vector genome) exists in a conformation having a high degree of secondary structure (FIGS. 8A and 8B, lanes 4–7), presumably due to intrastrand base-pairing. Furthermore, the half-complexity vector exists in this double-stranded form as early as 6 hours after infection (FIGS. 8A and 8B, lane 4), regardless of the presence or absence of adenovirus coinfection (FIGS. 8A and 8B, lane 3), whereas the full-size vector does not (FIG. 8A, lane 11).

Example 10

Density-based Fractionation of Vector Stocks in CsCl Gradients

In the vector preparations described above, the rAAV vectors were purified by bulk fractionation in CsCl followed by column chromatography. To analyze more highly purified vector preparations, additional preparations were produced and fractionated by density rather than by the bulk separation described in earlier examples.

Both the half-complexity and control full-size vectors were prepared as described above from five T225 flasks of C12 cells infected with adenovirus 5 (at a multiplicity of 10 infectious units per cell) and transfected with the vector plasmid (37.5 μg per flask). Benzonase®-treated lysates were prepared as described in Example 4, supra, and adjusted to a final refractive index of 1.3710 with CsCl. The lysates were transferred to a centrifuge tube, overlaid with 0.5 ml mineral oil and centrifuged in a Beckman ultracentrifuge in a swinging bucket rotor (SW41) at 35,000 rpm, 15° C. for 48 hours. Twenty-one fractions, of 200 μl each, were collected from each gradient. For each fraction, the refractive index was determined using an Abbe refractometer and the density was calculated from the refractive index value. Peak fractions were located by assaying each fraction to determine the particle titer (DRP) and infectivity (expressed as replication units, RU), then obtaining the particle:infectivity ratio. Analysis of the peak fractions for the half-complexity vector, compared to bulk-fractionated full-size vector, is shown in Table 4.

TABLE 4

Analysis of CsCl gradient fractions

| Sample | titer (DRP/ml) | titer (RU/ml) | Particle:Infectivity |
|---|---|---|---|
| rAAVGFP(0.5) CsCl fraction 11 | 2.01 × 10$^9$ | 2.02 × 10$^7$ | 100 |
| rAAVGFP(0.5) CsCl fraction 12 | 8.32 × 10$^9$ | 8.43 × 10$^7$ | 99 |
| rAAVGFP(0.5) CsCl fraction 13 | 8.81 × 10$^9$ | 9.55 × 10$^7$ | 92 |

TABLE 4-continued

Analysis of CsCl gradient fractions

| Sample | titer (DRP/ml) | titer (RU/ml) | Particle:Infectivity |
|---|---|---|---|
| rAAVGFP(0.5) CsCl fraction 14 | 3.41 × 10$^9$ | 2.08 × 10$^7$ | 164 |
| rAAVGFP(Sal) CsCl pool | 8.39 × 10$^9$ | 2.92 × 10$^7$ | 287 |

Peak fractions were analyzed further by gel electrophoresis to determine the conformation of vector DNA. Fractions with a density ranging from 1.362 g/ml to 1.394 g/ml were individually dialyzed, lysed and digested with SDS and proteinase K, incubated at 50° C. for 4 hours, extracted with phenol, phenol/chloroform, chloroform, precipitated with ethanol and loaded onto alkaline and neutral agarose gels, as described supra. Gels were denatured, neutralized, and blotted onto a nylon membrane; nucleic acids were crosslinked to the membrane, and the membrane was hybridized with a random-primed $^{32}$P-labeled GFP probe. Probed blots were exposed to film and phosphor screens. The results, shown in FIG. 9 (FIG. 9A shows a neutral gel and FIG. 9B shows an alkaline gel), indicate that the half-complexity vector exists in two conformations in the particles: either a single strand of half genome length (FIG. 9B, lanes 3–7) or a strand of full genome length which forms a duplex, each of whose strands is half genome length (FIG. 9A, lanes 3–7). The latter conformation of the rAAV-GFP(0.5) genomes are preferentially enriched in particles having a density similar to the density of particles containing the full-length rAAV-GFP (Sal) vector (compare FIG. 9A, lanes 3–5 with FIG. 9A, lanes 11 and 12).

Example 11

Expression in HeLa Cells by Density-fractionated rAAV Vectors

Transduction of human HeLa cells by half-complexity or full-size vectors, that had been prepared by density fractionation in CsCl gradients as described in Example 10, was examined. For comparison, half-complexity vectors that had been purified by the bulk CsCl and column chromatography method described in Example 4 were used. Negative controls were untransduced HeLa cells, and cells stably transduced with a GFP expression plasmid were used as positive controls. Transduction was assayed by measuring GFP expression by flow cytometry at 72 hours after infection. The results are presented in Table 5, where "% transduction" refers to the percentage of cells expressing GFP. These results show that the half-complexity vector transduces at least 20-fold more efficiently than a full-sized vector. In addition, higher expression levels were observed with half-complexity vectors from the denser fractions, consistent with enrichment, at these densities, for particles containing genomes that can rapidly form duplex molecules.

Expression of HeLa cells by density-fractionated rAAV vectors

| Vector | dose (DRP/Cell) | % transduction (n = 3) |
|---|---|---|
| Negative control | N/A | 0.04 |
| positive control | N/A | 95.1 |

-continued

Expression of HeLa cells by density-fractionated rAAV vectors

| Vector | dose (DRP/Cell) | % transduction (n = 3) |
|---|---|---|
| half-complexity column purified | 100 | 16.9 (+/−1.4) |
| | 1000 | 58.7 (+/−4.3) |
| half-complexity fraction 11 | 100 | 12.3 (+/−2.0) |
| | 1000 | 60.3 (+/−2.9) |
| half-complexity fraction 12 | 100 | 12.0 (+/−1.9) |
| | 1000 | 63.5 (+/−1.9) |
| half-complexity fraction 13 | 100 | 8.1 (+/−0.4) |
| | 1000 | 46.6 (+/−1.8) |
| half-complexity fraction 14 | 100 | 10.8 (+/−1.4) |
| | 1000 | 53.5 (+/−0.5) |
| full-size pool | 100 | 0.4 (+/−0.1) |
| | 1000 | 2.9 (+/−0.3) |

The results in this example indicate that higher expression levels of a transgene are obtained following infection of human cells with viruses containing a metabolically activated vector.

Taken together, the evidence in the foregoing examples demonstrates that expression in human cells is much more efficient with a vector that forms intrastrand base pairs (in this example, a half-complexity vector) than with a vector does not assume this structure.

Example 12

Production of a Half-complexity Vector From Stable Producer Cell Lines

A preferred method for producing rAAV vectors is to generate cells according to Clark et al. (1995) *Hum. Gene Therapy* 6:1329–1341; and U. S. Pat. Nos. 5,658,785; 5,858, 775. The aforementioned C12 cell lines contain an integrated rep and cap gene cassette and a stably integrated vector. When such cells are infected with adenovirus, the vector genome is excised, replicated and packaged into AAV capsids, which can be purified from lysates of infected cells.

A producer cell line was generated by transducing C12 cells (HeLa cells containing a rep-cap gene cassette, see also Example 4) with AAV-GFP(0.5) plasmid DNA, and a clone (KAO) was selected. This KAO-GFP clone was expanded into bulk cultures and used to generate rAAV-GFP(0.5) by infection with adenovirus type 5. In eight different preparations, the average yield was over 10,000 rAAV-GFP (0.5) particles per KAO-GFP cell. Thus, production of the vectors of the invention can be routinely accomplished on a commercial scale using a preferred method employing stable producer cell lines.

Example 13

In Vivo Expression of a Transgene Using a Metabolically Activated Vector

In this example, an rAAV vector polynucleotide encoding a fusion protein of tumor necrosis factor receptor (TNFR) and the constant region of an immunoglobulin molecule (Fc), denoted sTNFR(p75):Fc (ENBREL, Immunex) is produced according to the Examples above. The amino acid sequence for sTNFR(075):Fc is shown in FIG. 10; see U.S. Pat. 5,605,690.

A study is conducted using rAAV vector gene transfer in the streptococcus cell wall model of arthritis in rats. The rat model used in these studies is an art-accepted and FDA-accepted model for studying arthritis and is used for evaluating anti-cytokine therapies.

In this arthritis model, the disease is initiated by a single intraperitoneal (i.p.) injection of group A SCW peptidoglycan-polysaccharide (PG-APS) (30 µg body weight) into 4-week old (100 g) genetically susceptible female Lewis rats. Cromartie et al. (1977) *J. Exp. Med.* 146:1585–1602. Typically, this model exhibits a peripheral and symmetrical, biphasic polyarthritis with cycles of exacerbated recurrence and remission and is clinically and histologically similar to rheumatoid arthritis. An acute inflammation of the ankles, wrists and small joints of the feet develops within 24–48 hr, which persists for 4–5 days, and then partially resolves. This acute, neutrophil-predominant, inflammatory response is then followed by a spontaneously reactivating chronic inflammation at approximately day 15, which develops into a chronic, progressive, erosive synovitis. In addition to polyarthritis, this PG-APS model induces chronic granulomatous inflammation of the liver and spleen. The severity of arthritis (articular index, AI) is determined by scoring each ankle and wrist joint based on the degree of swelling, erythema, and distortion on a scale of 0–4 and summing the scores for all four limbs. In parallel, hind paw swelling can be measured by water displacement plethysmometry.

Month old female Lewis rats are injected i.p. with SCW, as described above. The rats are monitored daily for onset and disease progression by recording AI scores. As rats progress into the chronic phase of disease (day 14 to 15), they are divided into groups and administered various doses ($1\times10^7$–$1\times10^{12}$ DRPs) to the rear ankle joint.

Rats are inspected daily for disease onset and progression, and the severity of arthritis (AI) is recorded every 2 to 3 days as described above. The incidence and severity of disease in the AAVrTNFR-Fc, AAV control vector, and vehicle-treated groups is compared. Hind paw swelling is measured with a plethysmometer, and the number of involved paws (joint count) in each group is recorded and compared among the groups. Significance of difference among groups in the course of arthritis based on joint diameter measurements is analyzed by using an analysis of variance (ANOVA) statistical program. Statistical significance on gross-observation score is ascertained using the Student's unpaired t test.

Rats are sacrificed about 60 days after vector or vehicle administration. Animals from each of the AAVrTNFR-Fc vector-treated groups that show significant reduction in arthritis symptoms (>20% reduction in AI and in hind paw swelling) compared with AAV control vector- or vehicle-treated groups are kept alive and monitored for persistence of therapeutic efficacy for up to about 12 months.

The effect of vectors and vehicle treatments on joint morphology such as cartilage and bone resorption is assessed by X-ray radiography, and post-mortem by histopathological examination of hematoxylin and eosin (H/E)-stained joint cryosections. These sections are scored for hyperplasia of the synovial membrane, pannus formation, articular cartilage destruction and the production of massive fibrous tissue. Joint sections are also examined for evidence of leukocyte infiltration in the synovial space.

The presence of cell-mediated immune responses against AAVrTNFR-Fc-transduced cells is evaluated by isolating cells from the regional draining lymph nodes and spleen from a subset of animals, from which single-cell suspensions are made. T cell proliferation assays are performed using rTNFR-Fc fusion protein as a source of antigen. Cell-mediated cytotoxicity is tested using Chromium release assays with a stably-transfected rTNFR-Fc-expressing isogenic Lewis rat cell line (RT-1 compatible) as target.

Liver and spleen are examined for chronic granulomatous inflammation and the incidence and severity of disease will be compared among groups. In addition, other vital organs including lungs, heart GI tract and kidney are inspected for signs of pathology, followed by histopathological analyses of paraffin-embedded, H/E-stained tissue sections.

To examine the tissue distribution of vectors, DNA is prepared from all vital organs, ovaries and joints, and the presence of vector DNA is examined by Southern blot analyses using vector-specific probes and by PCR using vector-specific primers.

Serum samples from all animals are collected prior to, immediately following, and at weekly intervals after administration of vectors and vehicle are assayed for:

(i) Presence and levels of TNFR-Fc. An enzyme-linked immunoabsorbent assay (ELISA) measures total rTNFR-Fc serum levels, and a standard TNF-α bioassay measures rTNFR-Fc bioactivity.

(ii) Presence and levels of neutralizing antibodies directed against AAV capsid proteins by an ELISA to measure total levels anti-capsid antibodies, and by an anti-AAV capsid-mediated inhibition of AAV infectivity assay to test for the presence of anti-capsid neutralizing antibodies.

(iii) Presence and levels of neutralizing and/or non-neutralizing antibodies directed against rTNFR-Fc protein by an ELISA to measure total levels anti-rTNFR-Fc antibodies, and by a standard TNF-α bioassay to test for inhibition of rTNFR-Fc bioactivity. In this assay, serum samples are tested for inhibition of rTNFR-Fc protein activity (to block TNF-α from cell killing).

Although the foregoing invention has been described in some detail by way of illustration and example for purposes of clarity of understanding, it will be apparent to those skilled in the art that various changes and modifications can be practiced without departing from the spirit of the invention. Therefore the foregoing descriptions and examples should not be construed as limiting the scope of the invention.

What is claimed is:

1. A recombinant adeno-associated virus (rAAV) vector comprising a single-stranded heterologous nucleotide sequence comprising a region which forms intrastrand base pairs such that expression of a coding region of the heterologous sequence is enhanced relative to a second rAAV vector that lacks sufficient intrastrand base pairing to enhance said expression, wherein the region which forms intrastrand base pairs is in a coding region.

2. The rAAV vector of claim 1, wherein the sequence complexity of the heterologous sequence is about one-half of the length of the heterologous sequence, wherein the heterologous sequence forms a double-stranded structure along most or all of its length.

3. The rAAV vector of claim 2, further comprising an ITR flanked on both sides by heterologous sequences.

4. The rAAV vector of claim 1, wherein the coding region forms a double-stranded structure along most or all of its length.

5. The rAAV vector of claim 1, 2, 3, or 4, wherein said rAAV vector is capable of being packaged in an AAV particle.

6. A host cell comprising the rAAV vector of claim 1.

7. The host cell of claim 6, which is mammalian.

8. A host cell comprising the rAAV vector of claim 5.

9. The host cell of claim 8, which is mammalian.

10. A host cell comprising the rAAV vector of claims 2, 3, or 4.

11. The host cell of claim 10, which is mammalian.

12. A recombinant AAV particle comprising the rAAV vector of claim 1.

13. A recombinant AAV particle comprising the rAAV vector of claim 5.

14. A recombinant AAV particle comprising the rAAV vector of claim 2.

15. A recombinant AAV particle comprising the rAAV vector of claim 3 or 4.

16. A composition comprising the rAAV vector of claim 1.

17. The composition of claim 14, further comprising a pharmaceutical acceptable excipient.

18. A composition comprising the rAAV vector of claim 5.

19. The composition of claim 18, further comprising a pharmaceutically acceptable excipient.

20. A composition comprising the rAAV vector of claims 2, 3, or 4.

21. The composition of claim 20, further comprising a pharmaceutically acceptable excipient.

22. A method for preparing an rAAV vector according to claim 5 packaged in a particle, wherein the method comprises incubating a host cell under conditions that allow AAV replication and encapsidation, wherein said host cell comprises:

(a) an rAAV vector comprising a heterologous nucleotide sequence and one or more AAV inverted terminal repeat (ITR) sequences flanking said heterologous sequence, wherein the vector is less than about 2.5 kb, and (b) AAV rep function, AAV cap function, and helper virus function for AAV.

23. The method of claim 22 wherein rep arid cap functions are provided by a rep-cap cassette that is stably integrated in the host cell genome.

24. The method of claim 22 wherein rep and cap functions are provided by a plasmid.

25. The method of claim 22 wherein the rAAV vector is provided in a plasmid.

26. The method of claim 22, wherein the rAAV vector is stably integrated into the host cell genome.

27. The method of claim 22 wherein helper functions are provided by adenovirus infection.

28. A population of rAAV particles produced according to the method of claim 22.

29. A population of rAAV vectors produced according to the method of claim 22.

* * * * *

UNITED STATES PATENT AND TRADEMARK OFFICE
CERTIFICATE OF CORRECTION

PATENT NO.    : 6,596,535 B1                                         Page 1 of 1
DATED         : July 22, 2003
INVENTOR(S)   : Barrie J. Carter It is certified that error appears in the above-identified patent and that said Letters Patent is hereby corrected as shown below:

Column 3,
Line 11, please replace "Bems" with -- Berns --;
Line 24, please replace "RAAV" with -- rAAV --;

Column 31,
Line 66, please replace "AAVITR" with -- AAV ITR --.

Signed and Sealed this

Third Day of February, 2004

JON W. DUDAS
*Acting Director of the United States Patent and Trademark Office*